(12) United States Patent
Rush et al.

(10) Patent No.: US 9,173,654 B2
(45) Date of Patent: Nov. 3, 2015

(54) SYSTEM FOR TISSUE REPAIR

(71) Applicant: Raptor Surgical, LLC, Pleasanton, CA (US)

(72) Inventors: Shannon M. Rush, Pleasanton, CA (US); Sheriese Rush, Pleasanton, CA (US); Michael Yoon, Pleasanton, CA (US); Jim McCrea, Pleasanton, CA (US); Sosho Chang, Pleasanton, CA (US)

(73) Assignee: Raptor Surgical, LLC, Pleasanton, CA (US)

( * ) Notice: Subject to any disclaimer, the term of this patent is extended or adjusted under 35 U.S.C. 154(b) by 303 days.

(21) Appl. No.: 13/711,297

(22) Filed: Dec. 11, 2012

(65) Prior Publication Data

US 2014/0163583 A1 Jun. 12, 2014

(51) Int. Cl.
*A61B 17/04* (2006.01)
*A61B 17/11* (2006.01)
*A61B 17/02* (2006.01)
*A61B 17/06* (2006.01)
*A61B 17/29* (2006.01)

(52) U.S. Cl.
CPC ......... *A61B 17/0469* (2013.01); *A61B 17/0482* (2013.01); *A61B 17/0483* (2013.01); *A61B 17/1146* (2013.01); *A61B 17/0218* (2013.01); *A61B 2017/0472* (2013.01); *A61B 2017/0608* (2013.01); *A61B 2017/06042* (2013.01); *A61B 2017/1132* (2013.01); *A61B 2017/2937* (2013.01); *A61B 2017/2943* (2013.01)

(58) Field of Classification Search
CPC ........... A61B 17/0469; A61B 17/1146; A61B 2017/0472; A61B 17/0485; A61B 17/0491; A61B 2017/0498
See application file for complete search history.

(56) References Cited

U.S. PATENT DOCUMENTS

| | | |
|---|---|---|
| 1,577,054 A | 3/1926 | Berkmann |
| 2,264,679 A | 12/1941 | Ravel |
| 4,971,075 A | 11/1990 | Lee |
| 5,397,325 A | 3/1995 | Della Badia et al. |
| 5,766,234 A | 6/1998 | Chen et al. |
| RE36,020 E | 12/1998 | Moore et al. |
| 5,980,538 A | 11/1999 | Fuchs et al. |
| 6,117,144 A | 9/2000 | Nobles et al. |
| 6,136,010 A | 10/2000 | Modesitt et al. |
| 6,322,571 B1 | 11/2001 | Adams |
| 6,746,456 B2 | 6/2004 | Xiao |

(Continued)

FOREIGN PATENT DOCUMENTS

WO WO 2014/092863 6/2014

*Primary Examiner* — Gregory Anderson
(74) *Attorney, Agent, or Firm* — Levine Bagade Han LLP

(57) ABSTRACT

Systems for tissue repair are described where an elongate tissue repair device may be introduced into a single incision to access the damaged tissue. A suture delivery assembly may be sized for insertion through a single incision and positioned into proximity with a damaged or ruptured tissue region. A first portion of the damaged tissue region may be positioned within or along a channel defined along the suture delivery assembly and one or more lengths of suture may be secured to the first portion via the device. A second portion of the damaged tissue region may be similarly positioned within or along the channel and one or more additional lengths of suture may be secured to the second portion via the device. The first and second portions may then be approximated and secured to one another via the sutures to facilitate healing of the damaged tissue region.

29 Claims, 31 Drawing Sheets

(56) References Cited

U.S. PATENT DOCUMENTS

| | | |
|---|---|---|
| 6,921,408 B2 | 7/2005 | Sauer |
| 7,758,597 B1 | 7/2010 | Tran et al. |
| 8,123,102 B2 | 2/2012 | Manzo |
| 8,936,611 B2 | 1/2015 | Rush et al. |
| 2003/0167063 A1* | 9/2003 | Kerr .............................. 606/144 |
| 2003/0181925 A1 | 9/2003 | Bain et al. |
| 2007/0198037 A1 | 8/2007 | Deland |
| 2009/0138029 A1 | 5/2009 | Saliman et al. |
| 2009/0318958 A1 | 12/2009 | Ochiai |
| 2011/0313454 A1 | 12/2011 | Rush et al. |
| 2012/0239053 A1 | 9/2012 | Belliard et al. |
| 2014/0163584 A1 | 6/2014 | Rush et al. |
| 2015/0127026 A1 | 5/2015 | Rush et al. |

\* cited by examiner

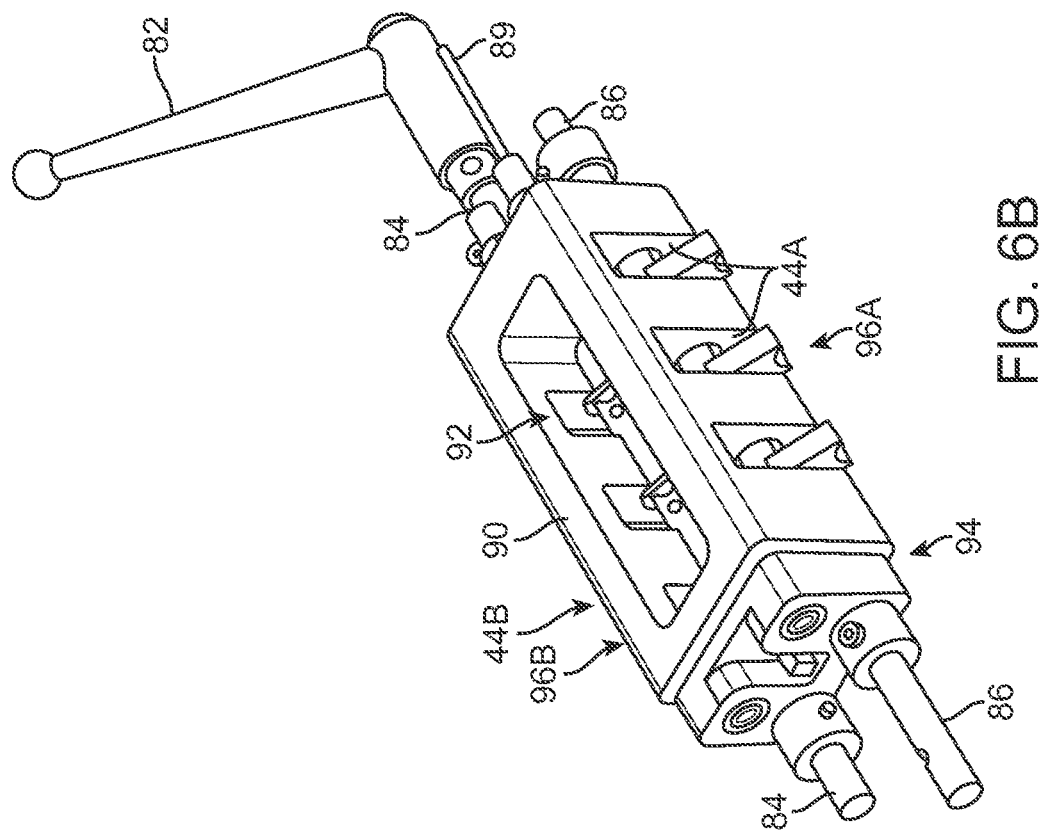
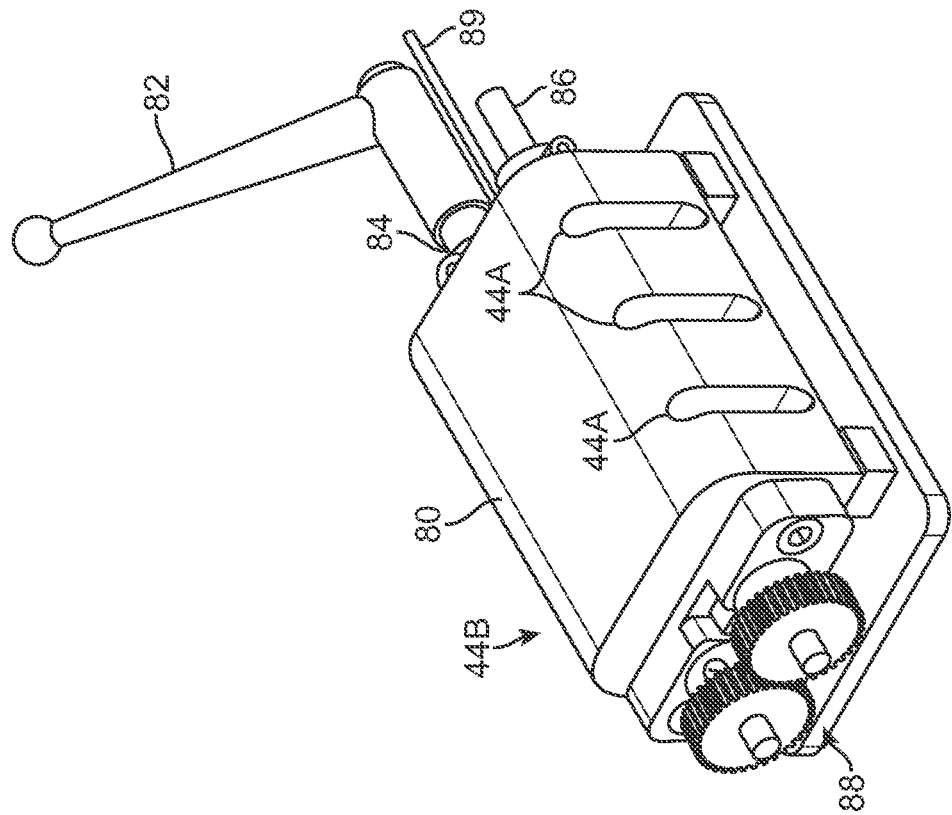
FIG. 6B
FIG. 6A

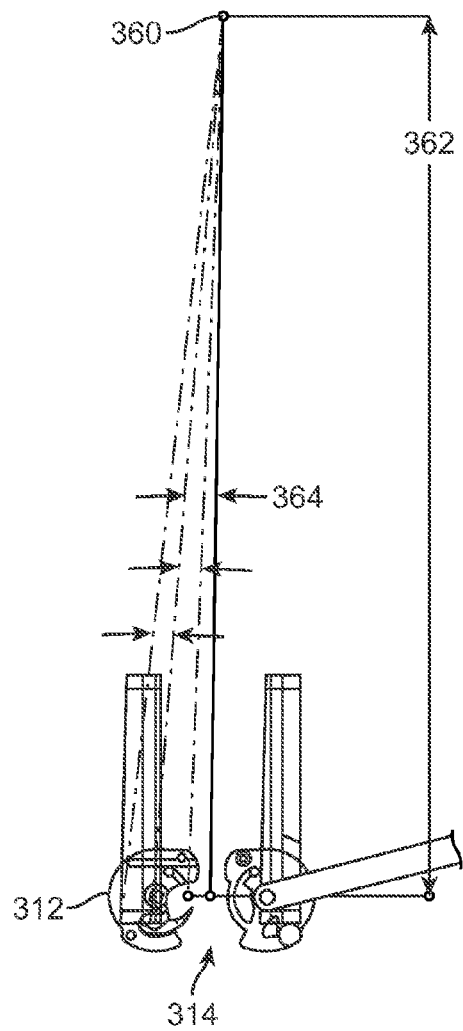
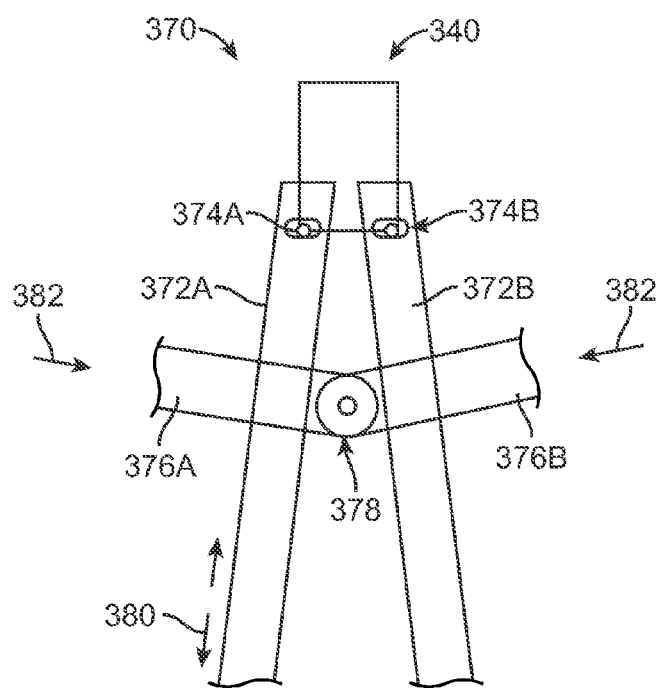
FIG. 26E
FIG. 26F

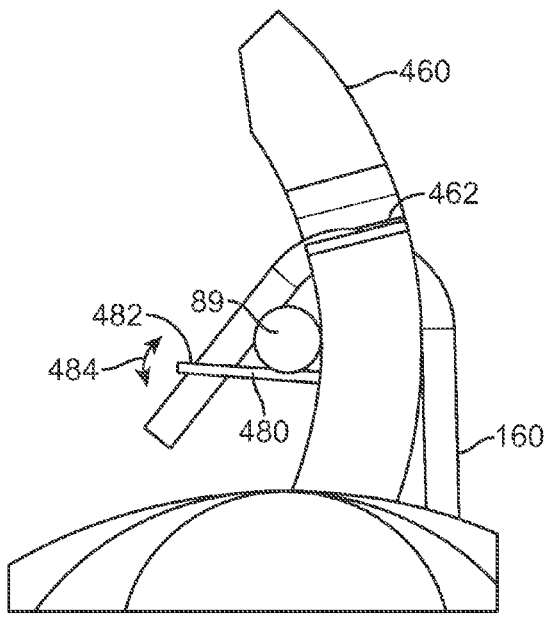
FIG. 35A
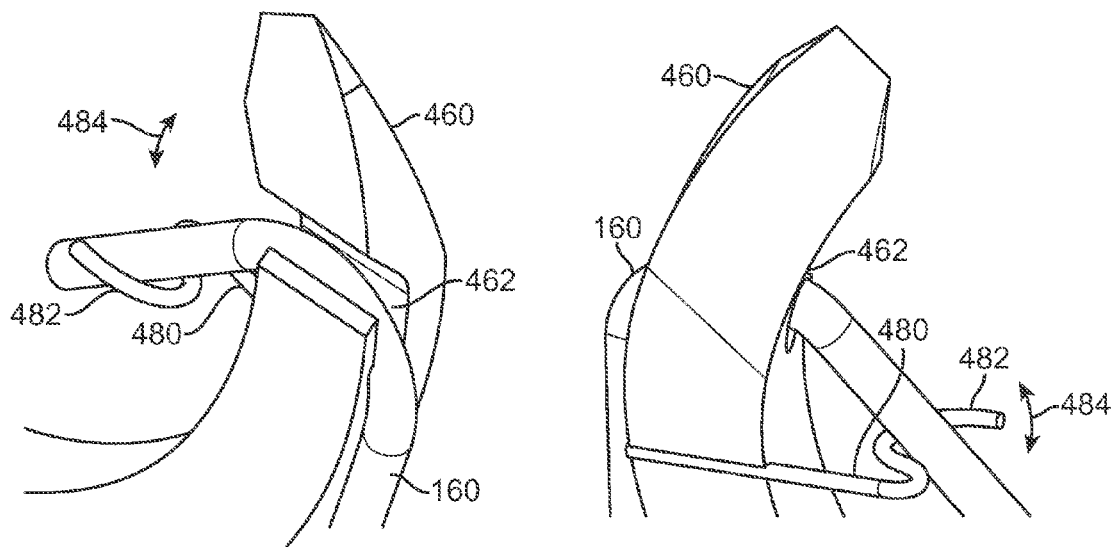
FIG. 35B
FIG. 35C

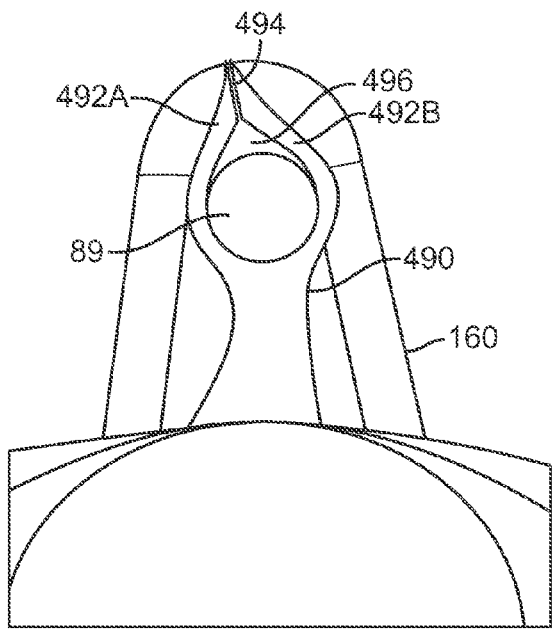
FIG. 36A
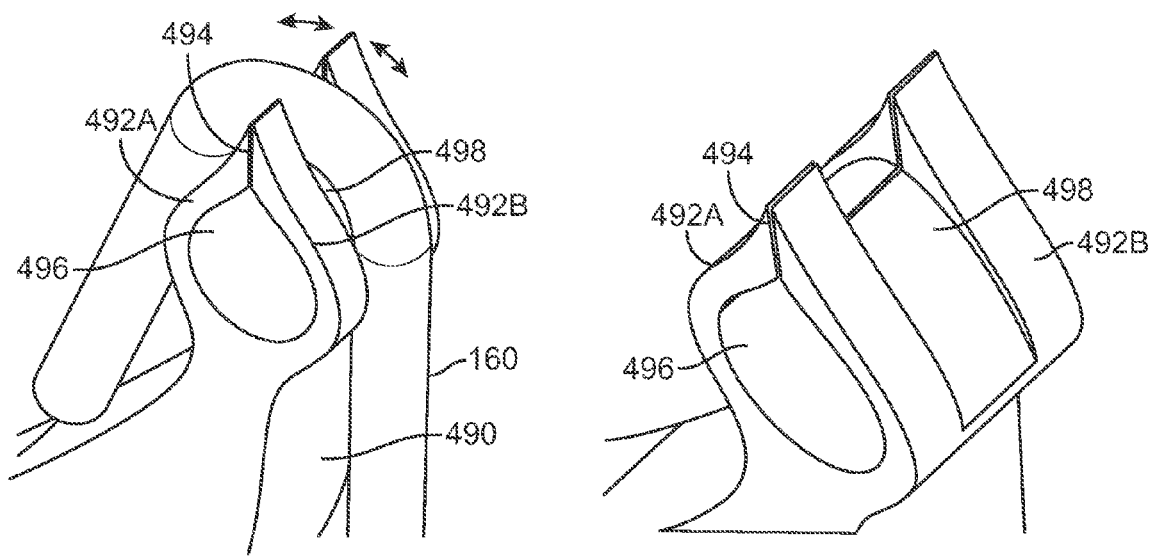
FIG. 36B
FIG. 36C

SYSTEM FOR TISSUE REPAIR

FIELD OF THE INVENTION

The present invention relates generally to medical devices and methods used for attaching soft tissues to one another. More particularly, the present invention relates to apparatus and methods for re-attaching a damaged tissue region to one another such as a ruptured Achilles tendon in a minimally invasive manner.

BACKGROUND OF THE INVENTION

Soft tissue damage, particularly tendon rupture such as the Achilles tendon, is typically a debilitating event. Surgical repair of a ruptured tendon generally requires the torn or ripped ends of the tendon, which are separated from one another, to be coapted by passing one or more sutures through each damaged end. Each of the torn ends are drawn towards one another by tightening of the sutures to restore the connecting muscles and tendon to their original lengths.

However, accessing the damaged tissue generally requires relatively large incisions or multiple smaller incisions for effecting adequate purchase and sufficient suturing of the damaged tendon to ensure proper healing of the tendon. Yet relatively large incisions or multiple incisions also increase the likelihood of infections and complications occurring.

Moreover, minimally invasive devices which may be inserted through relatively smaller incisions are generally limited in their application for repairing particular tissue regions. For instance, minimally invasive surgical instruments may enable a surgeon to pass sutures through tissue with the instruments introduced through relatively small incisions; however, these instruments are limited in their ability to pass multiple sutures through non-supported tissue structures in an efficacious manner.

Moreover, may such devices are insufficient in supporting tissue structures such as ruptured or torn tendons for minimally invasive surgical repair. Thus, tissue repair systems which are able to pass one or more sutures in a minimally invasive manner into tissue structures, such as the Achilles tendons, which are difficult to secure and manipulate are highly desirable.

BRIEF SUMMARY OF THE INVENTION

A suture delivery assembly may be sized for insertion through a single incision and positioned into proximity with a damaged or ruptured tissue region. Generally, one variation of such a tissue repair system may comprise a handle having an actuator, a suture delivery assembly coupled to the handle and defining a tissue receiving channel along the suture delivery assembly, one or more needles which are curved or arcuate and which are rotatable from a delivery position to a deployment position where the one or more needles are rotatable at least partially through the tissue receiving channel when articulated by the actuator, and one or more lengths of suture which carried by the one or more needles. Additionally, one or more stylets which are translatable through the suture delivery assembly may be inserted into proximity to the one or more needles where each of the needles may define a clearance slot which is sized to partially receive the one or more stylets when each of the one or more needles are aligned relative to one another in the deployment position.

In use for repairing a tissue region, generally a suture delivery assembly defining a tissue receiving channel therealong may be introduced through an incision in proximity to a ruptured or torn tissue and positioned relative to a first portion of the ruptured or torn tissue such that the tissue is positioned within the tissue receiving channel. The one or more needles within the suture delivery assembly may be rotated from a delivery position within the suture delivery assembly to a deployment position such that the one or more needles pierce into and through the damaged tissue positioned within the tissue receiving channel. As the one or more needles pierce through the tissue, one or more corresponding lengths of suture may be passed through the tissue via the needles.

Then, at least one stylet may be inserted through the suture delivery assembly and through at least one stylet clearance slot defined along the one or more needles to deliver a length of suture, which may be common with the suture passed through the tissue or which may be a separate length of suture. The needles may be retracted and the assembly removed leaving the one or more sutures behind in the tissue in a prescribed suturing pattern. The sutures may then be tightened to the tissue. This process may be repeated on a second portion of the ruptured or torn tissue and the resulting sutures from the second portion may be secured to the sutures from the first portion to reattach the ruptured tissue.

Examples of devices and methods which may be used with the devices and methods described herein are further disclosed in detail in U.S. patent application Ser. No. 13/113,505 filed May 23, 2011 (U.S. Pub. 2011/0313454 A1) and U.S. Prov. App. 61/349,025 filed May 27, 2010, each of which is incorporated herein by reference in its entirety for any purpose.

In one example, a tissue repair assembly may have a handle housing and an actuator which is actuatable and is operatively coupled to a suture delivery assembly designed for percutaneous insertion through an incision. The suture delivery assembly may be sized for subcutaneous placement while contacting the underlying tissue to be treated. The assembly may have a height, e.g., of less than 2 cm, a width, e.g., of less than 3 cm, and a length, e.g., of less than 7 cm. The suture delivery assembly has an atraumatic distal end and external shell assembly comprised of a first portion of external shell attachable to a second portion of the external shell both which may surround a needle housing assembly. The suture delivery assembly may be generally configured to define a tissue receiving portion for contacting the tissue to be treated where the tissue receiving portion faces away from the handle housing.

The needle assembly itself may be comprised of a first set needles, e.g., three curved or arcuate needles, which are positioned adjacent to one another and a second set of needles, e.g., three curved or arcuate needles which are also positioned adjacent to one another. Each of the first set of needles and second set of needles may be positioned in apposition to one another such that each needle is staggered relative to one another. Moreover, each of the first and second set of needles may be rotatably positioned within the needle housing assembly to rotate relative to the housing assembly and traverse through the tissue receiving portion for piercing through and passing suture through the contacted tissue.

In one example of use such as with a ruptured or torn tendon such as the Achilles tendon, a single incision, e.g., less than 3 cm in length, may be made in the patient leg in proximity to or between the torn tissue portions. Because the suture delivery assembly may have a housing volume, e.g., of less than 17 cc to 30 cc, the assembly may be inserted through the incision, e.g., up to an insertion distance of less than 5 cm, such that the tissue receiving channel may contact the first portion of tissue, e.g., a proximal portion of a ruptured Achilles tendon. Because the channel diameter may be sized or adjusted, e.g., between 0.5 cm to 2 cm, to accommodate various size tissue diameters, the damaged first portion of tissue may be securely retained by the assembly which may pass the needles through the tissue to deliver one or more lengths of suture in proximity to the first ruptured segment.

Once the tissue has been positioned and/or temporarily secured within or against the tissue repair assembly, the handle may be actuated to rotate respective actuation shaft upon which the needles are secured in opposing directions which in turn rotates each of the needle assemblies from within the housing assembly and into and through the tissue. As each of the needles pass through the tissue, they may each pass portions of a common length of suture entirely through the tissue. Moreover, the distal tips of each of needle may rotate through the tissue receiving channel (and through any tissue present) to converge along or in proximity to a common longitudinal axis along the assembly. Once the needles have passed their respective portions of suture through the tissue, a stylet may then pass a terminal suture end (or another length of suture) through each of the suture portions aligned along or in proximity to the common longitudinal axis for further tightening and securement.

With the first portion of tissue secured, the tissue repair assembly may be removed from the incision and the same suture delivery assembly with additional lengths of suture (or a second assembly) may be re-introduced in the opposing direction through the incision to contact the second portion of tissue, e.g., the distal portion of ruptured tendon. The suture delivery assembly may then be secured to the second portion of tissue with the resulting second suture configuration in proximity to the second ruptured segment. The suture delivery assembly may then be removed and the terminal ends of the first suture and second suture configuration may be tied to one another through the incision to approximate and secure the first ruptured segment and second ruptured segment against one another to facilitate healing.

Each of the needles may be arcuate or otherwise curved, e.g., in a semi-circular manner, such that each of the needles may be positioned entirely within the needle housing assembly during initial insertion and placement within the tissue. The curvature of the needle may allow for the needles to be rotated within a plane which is transverse to a longitudinal axis of the housing assembly such that the needle may be rotated through an angle of needle engagement, e.g., 120° or more. This allows for the needle proximal end to be driven for the needle piercing tip to be rotated from an enclosed position to one where the distal piercing tip of the needle is advanced through a corresponding needle opening defined along tissue receiving channel and into a needle receiving channel. As the piercing tip passes through the tissue receiving channel along a circular needle trajectory, each piercing tip of each needle may pass a length of suture through the tissue. The position of the housing assembly 22 be maintained relative to the tissue to be treated via the handle attachment.

The tissue receiving channel may be varied in size or adjusted to facilitate temporarily clamping upon the tissue but may generally have a diameter of about 1.25 cm in one variation. Moreover, the diameters of the curved needles may also vary but generally may range anywhere from, e.g., 1 cm to 1.5 cm, in this and other variations. Additionally, each of the needles may be advanced simultaneously, e.g., each of the first and second needle assemblies along both sides may be advanced through the tissue at the same time. Alternatively, the needles may be deployed sequentially along either side (e.g., sequentially along a single side) or both sides (e.g., sequentially along alternating sides) or any other number of deployment sequences depending upon the desired sequence of needle deployment. Moreover, the order of needle deployment may be varied in this variation as well as any of the other variations described herein. Furthermore, the stylet channel may be defined through the length of the housing where the stylet channel is coincident with the longitudinal axis in proximity to where each of the needle distal tips converges.

The needle piercing tips may further define a stylet clearance slot defined along each needle body proximal to the piercing tip. The stylet clearance slot provides for passage of the stylet in proximity to the deployed needles when the stylet is used to pass the suture through the suture loops passed by each needle through the tissue.

In another, an adjustable housing assembly may have two adjacent housing assemblies defining a tissue receiving channel therebetween. The housing assemblies may be movably adjusted relatively away or towards one another to accommodate various size tissues to be treated. Moreover, the adjustability of the housing assemblies may also allow for the tissue to be stabilized relative to the housing assemblies by temporarily clamping the assemblies upon the tissue while the needles and suture are driven into and through the tissue.

Once the repair device has been inserted in proximity to the tissue region to be treated, the housing may be articulated via actuation handles such that the housing pivots about the one or more biasing members to place the presentation surfaces defining the tissue receiving channel securely around the tissue of interest. With the tissue positioned within the tissue receiving channel, the housing positioning relative to the tissue may be further adjusted, if so desired. Each of the needles may have one or more lengths of suture positioned along each needle body and between each adjacent needle. Once the device has been desirably positioned relative to the tissue, the needles may be actuated (simultaneously or sequentially, as described herein) such that the needles are rotated by the actuation shafts. The piercing tips of the needles may accordingly exit the needle openings defined along the presentation surfaces and traverse through the tissue receiving channel in a circular curve or arc trajectory.

As the needles traverse through the channel and tissue, the needles may pass the suture loops through the tissue and into proximity to the stylet channels defined longitudinally through respective housing. As previously described, the needles may define a notched or cut-out section as a stylet clearance slot which aligns with the stylet channels when the needles have been fully rotated into their deployed configuration. Once the needles have carried the suture lengths and suture loops through the tissue and into proximity to the stylet channels, the stylet (which carries a length of the suture) may accordingly be passed through the stylet channel to route the suture through the suture loops for further tightening of the suture upon the tissue. Once the suture loops have been passed via the needles, the needles may be retracted proximally back through the tissue and into the housing for disengaging the tissue and subsequent removal of the device from the tissue region.

Turning now to the needle assemblies, the number and relative positioning of the needles may be varied. Although the needles may be in a staggered and alternating configuration, the needles may be more closely aligned such that the needle tips are immediately adjacent to one another. Alternatively, the needles may be arranged in a staggered configuration farther apart from one another depending upon the desired suturing pattern.

Regardless of the number of needles used and the relative positioning of the needles, the needles may be configured and positioned relative to the tissue receiving channel such that the needles may penetrate into and through any number of varying tissue sizes. Regardless of the tissue size, the tissue may be positioned within the tissue receiving channel such that when the needle is deployed, its piercing tip may enter the tissue through a tissue entry along a side portion of the tissue and pierce through the tissue at a tissue exit located along a top portion of the tissue where the side and top are relative to the tissue position relative to the tissue receiving channel.

The needle may pass a length of suture carried via the suture guide exit entirely through the tissue regardless of tissue size. With the suture passed through, the stylet may be introduced through the suture loop formed by the suture and left when the needle piercing tip is retracted and the suture falls out of the suture guide exit.

BRIEF DESCRIPTION OF THE DRAWINGS

FIG. 6A illustrates another variation of the suture delivery assembly.

FIG. 6B illustrates yet another variation of the suture delivery assembly having a relatively smaller housing.

FIG. 26E schematically illustrates the rotational range of movement of the suture delivery assembly for adjustment upon the tissue to be treated.

FIG. 26F schematically illustrates an example of a mechanism for translating an actuation force into a clamping force upon the tissue to be treated.

FIGS. 35A to 35C illustrate front and perspective views of another needle variation showing a needle having a flexible suture guidance arm.

FIGS. 36A to 36C illustrate front and perspective views of yet another needle variation of a needle having a split piercing tip.

DETAILED DESCRIPTION OF THE INVENTION

Ruptured or torn tendons in particular may be difficult to repair due to the fibrous and relative toughness of these tissues. Additionally, ruptured or torn tendons may be unsupported within the body thus requiring the securement and approximation of the torn edges towards one another. A suture delivery assembly may be sized for insertion through a single incision and positioned into proximity with a damaged or ruptured tissue region. A first portion of the damaged tissue region may be positioned within or along a channel defined along the suture delivery assembly and one or more lengths of suture may be secured to the first portion via the device. A second portion of the damaged tissue region may be similarly positioned within or along the channel and one or more additional lengths of suture may be secured to the second portion via the device. The first and second portions may then be approximated and secured to one another via the sutures to facilitate healing of the damaged tissue region.

Although described in reference to the suturing and repair of tendons, particularly the Achilles tendon, the devices and methods described herein may be utilized on other tissue regions. Moreover, examples of such devices and methods of use are further described in detail in U.S. patent application Ser. No. 13/113,505 filed May 23, 2011 (U.S. Pub. 2011/0313454 A1) and U.S. Prov. App. 61/349,025 filed May 27, 2010, each of which is incorporated herein by reference in its entirety for any purpose.

Figure 1:
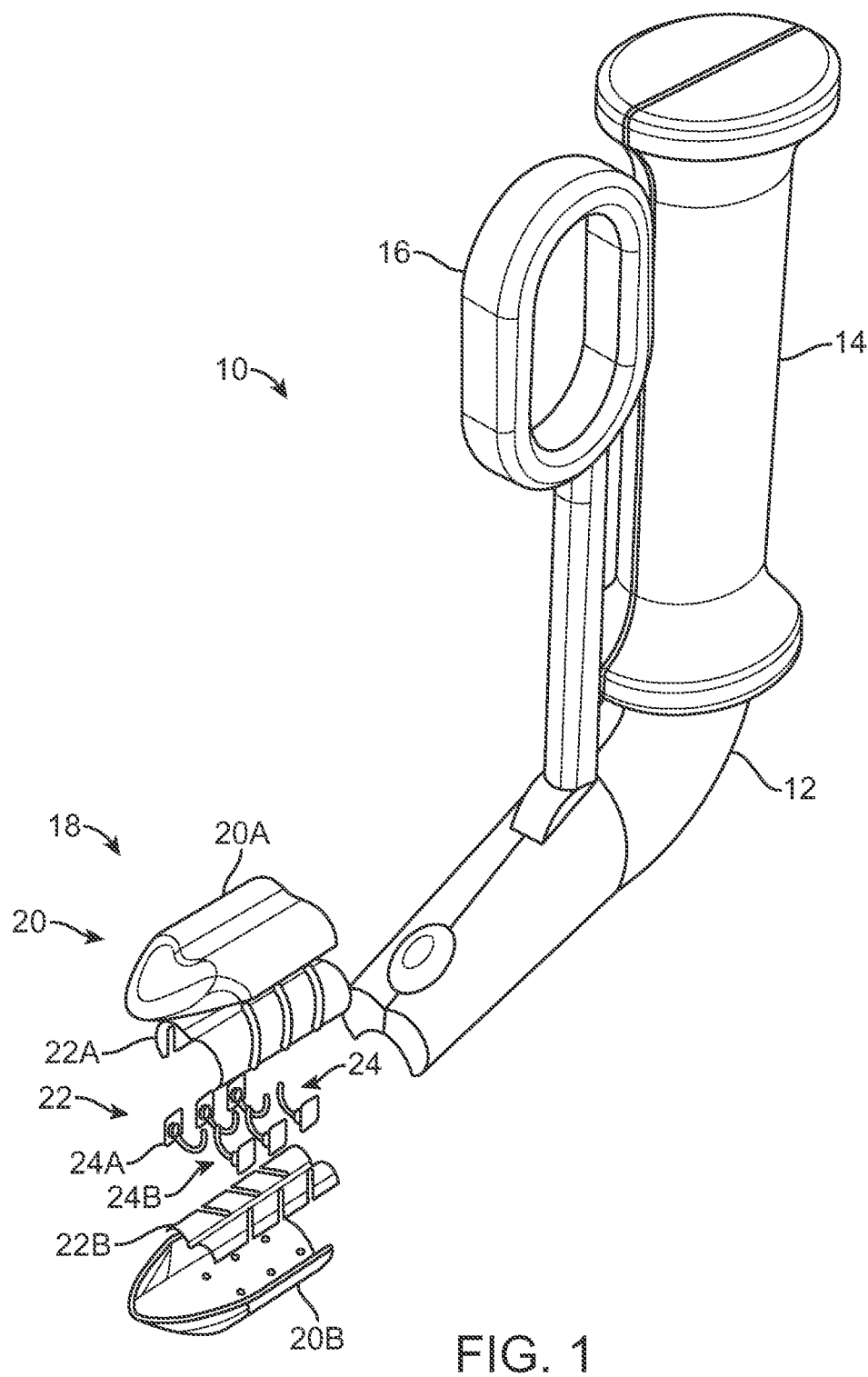
FIG. 1 illustrates a perspective view of an exploded suture delivery assembly attachable to a handle.

Turning now to the perspective view of FIG. 1, an example of a tissue repair assembly 10 is illustrated having a handle housing 12 and handle grip 14. An actuator 16 is actuatable relative to the housing 12 and is operatively coupled to a suture delivery assembly 18 which is designed for percutaneous insertion through an incision. The suture delivery assembly 18 may be sized for subcutaneous placement while contacting the underlying tissue to be treated. Hence, the assembly 18 may have a height, e.g., of less than 2 cm, a width, e.g., of less than 3 cm, and a length, e.g., of less than 7 cm. The suture delivery assembly 18 has an atraumatic distal end and external shell assembly 20 comprised of a first portion of external shell 20A attachable to a second portion of external shell 20B both which may surround a needle housing assembly 22. The suture delivery assembly 18 may be generally configured to define a tissue receiving portion for contacting the tissue to be treated where the tissue receiving portion faces away from the handle housing 12 in one variation, as described below in further detail.

The needle housing assembly 22 may be comprised of a first portion of needle housing 22A and a second portion of needle housing 22B, in one variation, which may at least partially enclose a needle assembly 24. The needle assembly 24 itself may be comprised of a first set needles 24A, e.g., three curved or arcuate needles, which are positioned adjacent to one another and a second set of needles 24B, e.g., three curved or arcuate needles which are also positioned adjacent to one another. Each of the first set of needles 24A and second set of needles 24B may be positioned in apposition to one another such that each needle is staggered relative to one another. Moreover, each of the first and second set of needles 24A, 24B may be rotatably positioned within the needle housing assembly 22 to rotate relative to the housing assembly 22 and traverse through the tissue receiving portion for piercing through and passing suture through the contacted tissue, as described in further detail below.

Figure 2A:
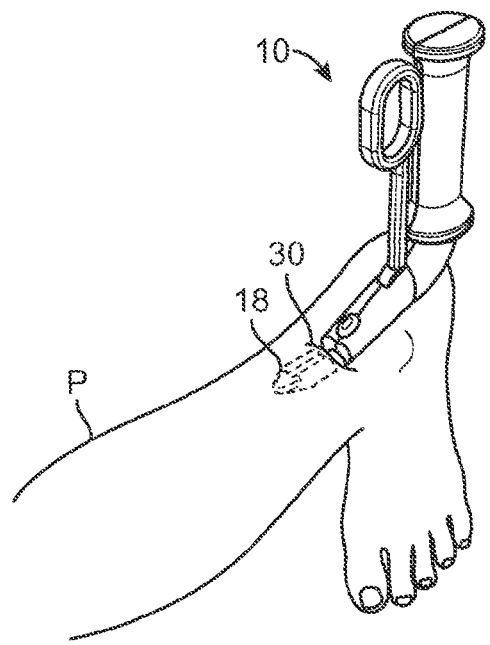
FIGS. 2A and 2B illustrate an example of how a suture delivery assembly may be introduced percutaneously for attaching one or more sutures to a first portion of a damaged or ruptured tendon.
Figure 2B:
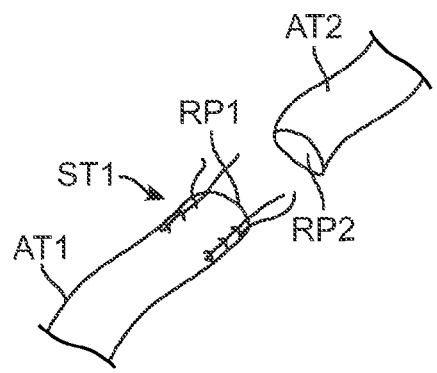
Figure 2C:
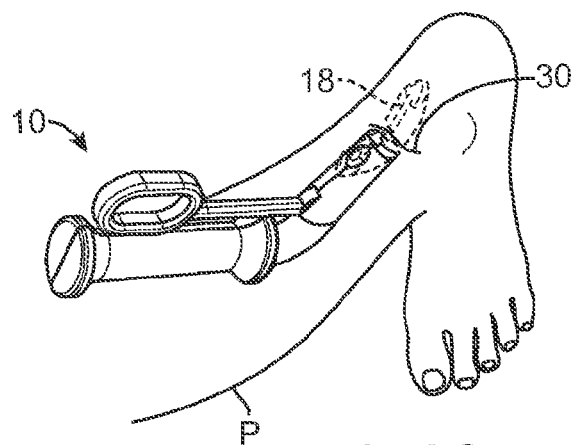
FIGS. 2C to 2E illustrate how the suture delivery assembly may be used for attaching one or more sutures to a second portion of a damaged or ruptured tendon and how the damaged ends may be approximated and secured to one another.

In one example of use such as the repair of soft tissue, FIGS. 2A and 2C illustrate how the tissue repair assembly 10 may be utilized. In the example of a ruptured or torn tendon such as the Achilles tendon, a single incision 30, e.g., less than 3 cm in length, may be made in the patient leg P in proximity to or between the torn tissue portions. Because the suture delivery assembly 18 may have a housing volume, e.g., of less than 17 cc to 30 cc, the assembly may be inserted through the incision 30, e.g., up to an insertion distance of less than 5 cm, such that the tissue receiving channel may contact the first portion of tissue AT1, e.g., a proximal portion of a ruptured Achilles tendon. Because the channel diameter may be sized or adjusted, e.g., between 0.5 cm to 2 cm, to accommodate various size tissue diameters, the damaged first portion of tissue AT1 may be securely retained by the assembly 18 which may pass the needles through the tissue AT1 to deliver one or more lengths of suture in proximity to the first ruptured segment RP1.

Once the tissue has been positioned and/or temporarily secured within or against the tissue repair assembly 10, the handle may be actuated to rotate respective actuation shaft upon which the needles are secured in opposing directions which in turn rotates each of the needle assemblies from within the housing assembly and into and through the tissue. As each of the needles pass through the tissue, they may each pass portions of a common length of suture entirely through the tissue. Moreover, the distal tips of each of needle may rotate through the tissue receiving channel (and through any tissue present) to converge along or in proximity to a common longitudinal axis along the assembly. Once the needles have passed their respective portions of suture through the tissue, a stylet may then pass a terminal suture end (or another length of suture) through each of the suture portions aligned along or in proximity to the common longitudinal axis for further tightening and securement.

The manner in which the suture lengths are passed through the tissue and secured may be utilized in each of the variations described herein and are not limited to any particular embodiment. FIG. 2B illustratively shows the ruptured first portion of tissue AT1 with the resulting first suture configuration ST1 secured to the tissue by the delivery assembly 18.

Figure 2D:
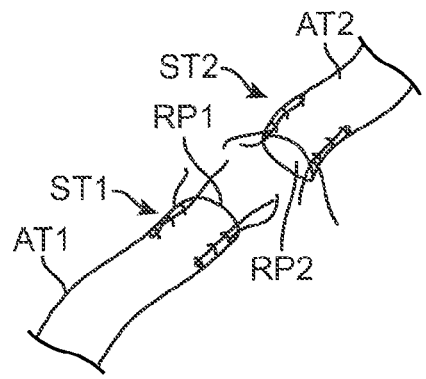
Figure 2E:
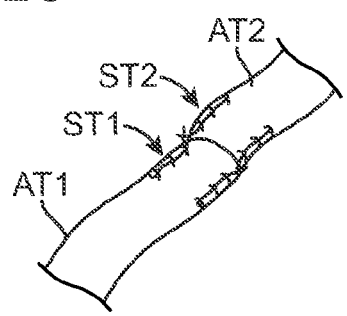

With the first portion of tissue AT1 secured, the tissue repair assembly 10 may be removed from the incision 30 and the same suture delivery assembly 18 with additional lengths of suture (or a second assembly) may be re-introduced in the opposing direction through the incision 30 to contact the second portion of tissue AT2, e.g., the distal portion of ruptured tendon, as shown in FIG. 2C. The suture delivery assembly 18 may then be secured to the second portion of tissue AT2 with the resulting second suture configuration ST2 in proximity to the second ruptured segment RP2, as shown in FIG. 2D. The suture delivery assembly 18 may then be removed and the terminal ends of the first suture ST1 and second suture configuration ST2 may be tied to one another through the incision 30 to approximate and secure the first ruptured segment RP1 and second ruptured segment RP2 against one another to facilitate healing, as shown in FIG. 2E.

Figure 3:
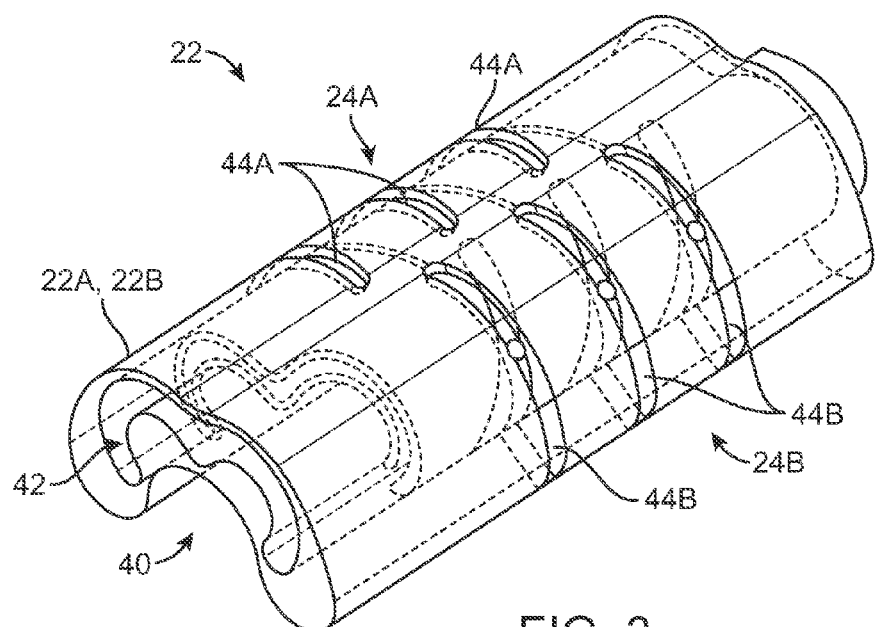
FIG. 3 illustrates a detailed perspective view of another variation of the suture delivery assembly.

Various embodiments of the suture delivery assembly and needle housing assembly may be utilized. Another example is illustrated in the perspective view of FIG. 3 which shows a partial cross-sectional needle housing assembly 22 (for clarity) having a curved outer surface symmetrically configured around a tissue receiving channel 40 which may be semi-circular in cross-section or curved into a receiving portion for contacting and at least partially enveloping the tissue to be sutured. The housing assembly 22 may curve into a flared configured which defines the tissue receiving channel 40 such that the first needle assembly 24A is aligned along a first side of the housing assembly 22 and the second needle assembly 24B is aligned along a second side of the housing assembly 22 such that each of the needles are aligned to follow a corresponding needle guide 44A, 44B such that the needles may rotate along a curved needle channel 42 within the housing assembly 22.

Although three needles 24A are shown positioned along the first side of housing assembly 22 and three needles 24B are shown positioned along the second side of housing assembly 22, additional needles may also be utilized as practicable depending upon the tissue region to be treated.

Figure 4A:
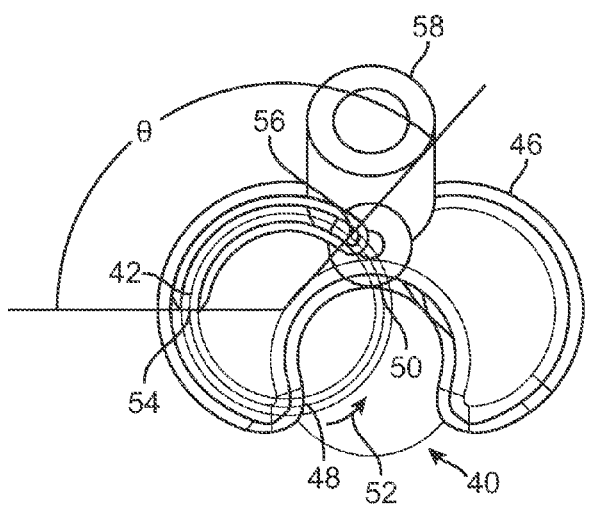
FIGS. 4A and 4B illustrate end views of variations of the suture delivery assembly.

Each of the needles may be arcuate or otherwise curved, e.g., in a semi-circular manner, such that each of the needles may be positioned entirely within the needle housing assembly 46 during initial insertion and placement within the tissue. The curvature of the needle may allow for the needles to be rotated within a plane which is transverse to a longitudinal axis of the housing assembly 22 such that the needle may be rotated through an angle of needle engagement Θ, e.g., 120° or more, as shown in the partial cross-sectional end view of FIG. 4A. This allows for the needle proximal end 56 to be driven for the needle piercing tip 54 to be rotated from an enclosed position to one where the distal piercing tip 54 of the needle is advanced through a corresponding needle opening 48 defined along tissue receiving channel 40 and into a needle receiving channel 50. As the piercing tip 54 passes through the tissue receiving channel 40 along a circular needle trajectory 52, each piercing tip 54 of each needle may pass a length of suture through the tissue. The position of the housing assembly 22 may be maintained relative to the tissue to be treated via the handle attachment 58.

Figure 4B:
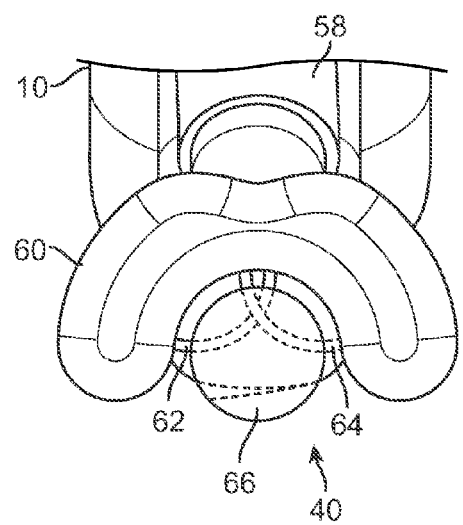

Another variation of the needle housing assembly 60 is illustrated in the end view of FIG. 4B which shows a curved and flared housing assembly 60 with a tissue of interest 66 being treated while positioned along the tissue receiving channel 40. At least a first needle 62 and a second needle 64 are shown as having been advanced from the housing assembly 60 and rotated through tissue 66 along respective opposing side portions and out through a portion of the tissue between the needles and along the receiving channel 40 while carrying lengths of suture along each needle through the tissue for securement. The tissue receiving channel 40 may be varied in size or adjusted to facilitate temporarily clamping upon the tissue but may generally have a diameter of about 1.25 cm in one variation. Moreover, the diameters of the curved needles may also vary but generally may range anywhere from, e.g., 1 cm to 1.5 cm, in this and other variations.

Each of the needles may be advanced simultaneously, e.g., each of the first and second needle assemblies along both sides may be advanced through the tissue at the same time. Alternatively, the needles may be deployed sequentially along either side (e.g., sequentially along a single side) or both sides (e.g., sequentially along alternating sides) or any other number of deployment sequences depending upon the desired sequence of needle deployment. Moreover, the order of needle deployment may be varied in this variation as well as any of the other variations described herein.

Figure 5A:
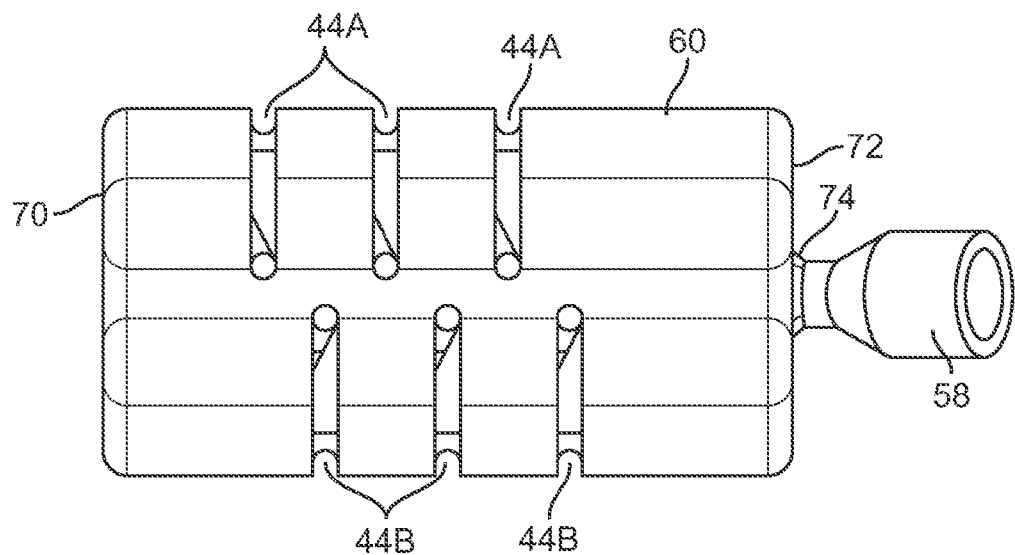
FIGS. 5A to 5C illustrate respective top, side, and end views of another variation of the suture delivery assembly.
Figure 5B:
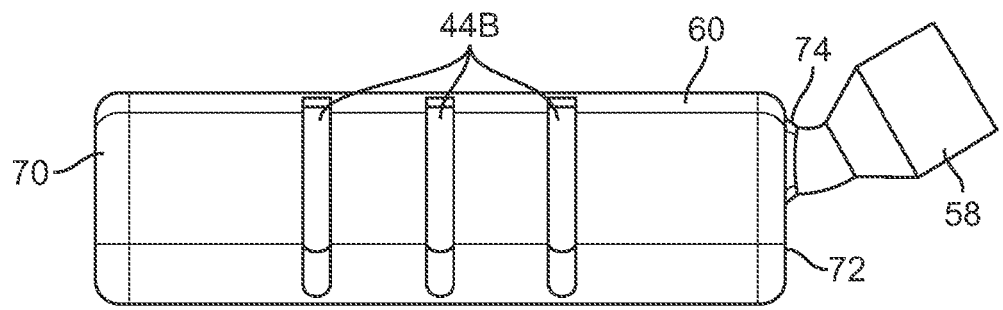
Figure 5C:
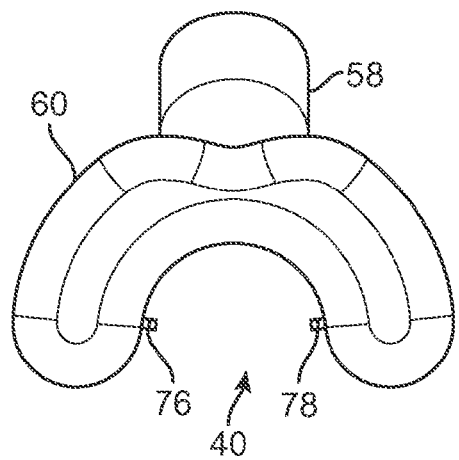

FIGS. 5A to 5C illustrate top, side, and end views, respectively, of yet another variation of the housing assembly 60. The distal end 70 is shown as having an atraumatic blunt end as well as the proximal end 72 which is connected to handle attachment 58 to the housing assembly 60 via attachment 74. Each of the curved needles may travel along a corresponding needle guide 44A, 44B and they may be arranged in a staggered pattern which allows for the distal tips of each needle to cross one another such that the lengths of suture carried by each needle may be secured to one another after being passed through the tissue. The partial cross-sectional end view of FIG. 5C illustrates how the needles may be advanced into the tissue receiving channel through respective needle openings 76, 78.

FIG. 6A illustrates a perspective view of yet another variation of the tissue repair assembly with a needle housing assembly 80 which is relatively flat. In this variation, two actuation handles may be used to actuate the needle assemblies. A single actuation handle 82 is illustrated as being attached to needle actuation shaft 84 and a second actuation handle is shown removed from needle actuation shaft 86 for clarity. An exposed actuation assembly 88 is also illustrated on a distal end of the device also for clarity. In this variation, a single stylet 89 which may hold a length of suture, such as a free end of the suture which is passed through the tissue via the needle assemblies, may be advanced through the needle housing assembly 80 and between each of the needle ends after being passed through the tissue. The stylet 89 may thus pass the suture through loops of suture passed through and engaged to the tissue for further tightening and/or securement to the corresponding suture on the apposed damaged tissue.

Figure 7A:
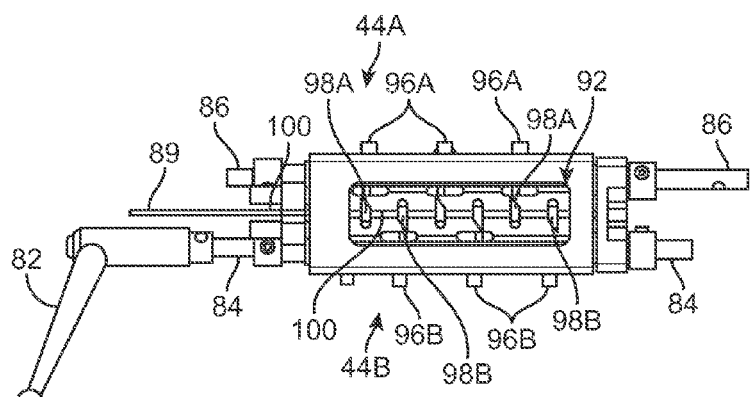
FIGS. 7A to 7C illustrate respective top, side, and bottom views of a variation of the suture delivery assembly.
Figure 7B:
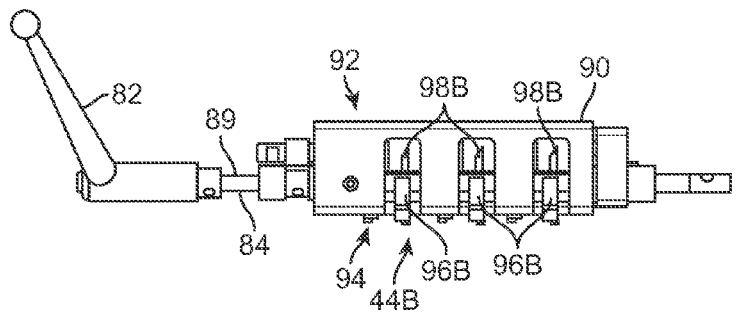

FIG. 6B shows yet another variation of the needle housing assembly 90 which may have a housing which is relatively smaller in size and width than the variation of FIG. 6A. In this example, the needle receiving channel 92 is illustrated as housing the first needles 96A and second needles 96B positioned in apposition relative to one another. FIGS. 7A to 7C illustrate respective top, side, and bottom views of the tissue repair assembly and further shows each of the needles 96A, 96B having respective first piercing tips 98A and second piercing tips 98B in their deployed configuration where the needles 96A, 96B have been rotated from their delivery position from within the housing. With the tissue receiving channel 94 positioned along the bottom of the housing assembly 90 for contact against the tissue to be secured, the first and second piercing tips 98A, 98B may rotate through the channel 94 (and through any tissue present) to converge along or in proximity to the common longitudinal axis of the assembly as indicated by the stylet channel 100. The stylet 89 carrying a suture length may be passed through each respective suture loop carried by each needle passed through the tissue.

Figure 7D:
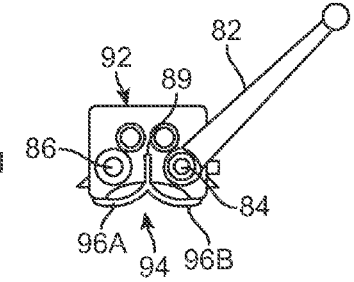
FIGS. 7D and 7E illustrate respective end views of the assembly of FIGS. 7A to 7C.
Figure 7C:
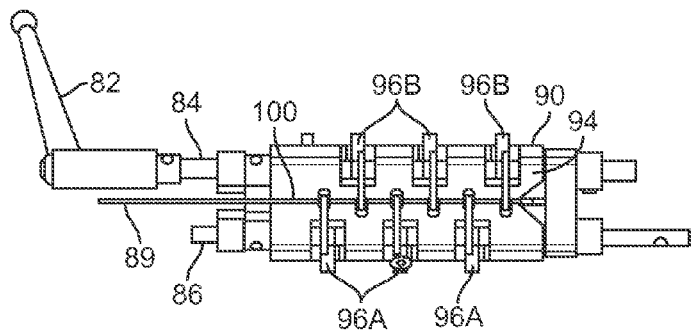
Figure 7E:
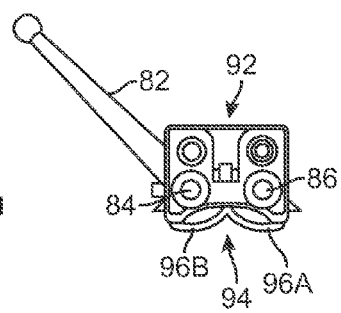

FIGS. 7D and 7E illustrate proximal and distal end views of the assembly to show how the one or more handles (only one handle 82 is shown for clarity) may be rotated to actuate the rotation of the respective shafts 84, 86 which in turn rotates each of the needles 96A, 96B. The convergence of the needle tips along with any lengths of suture carried by the needles may be seen particularly converging upon or in proximity to the stylet channel 100 through which stylet 89 may be translated.

Figure 8A:
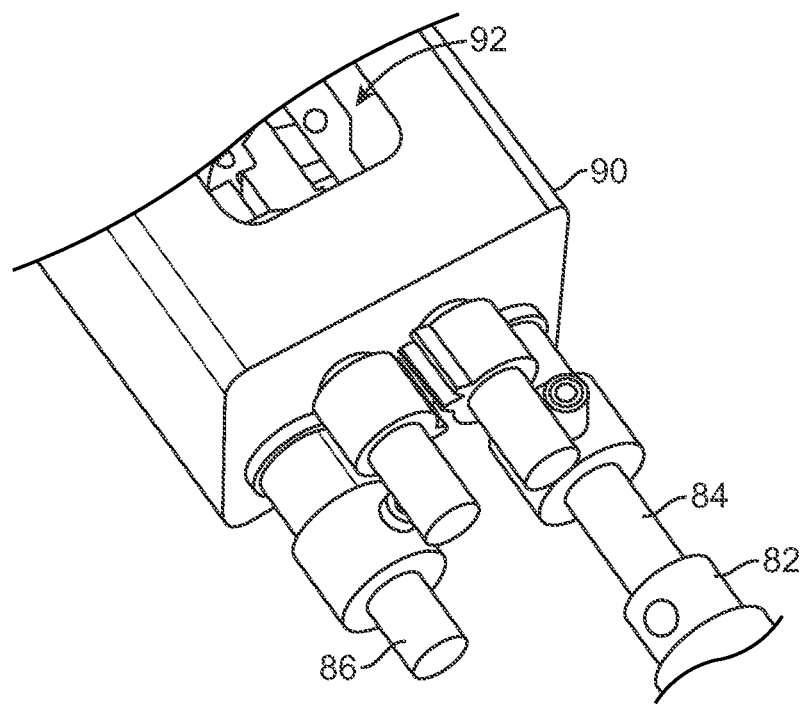
FIGS. 8A and 8B illustrate perspective views of the proximal and distal ends of the assembly of FIGS. 7A to 7C.
Figure 8B:
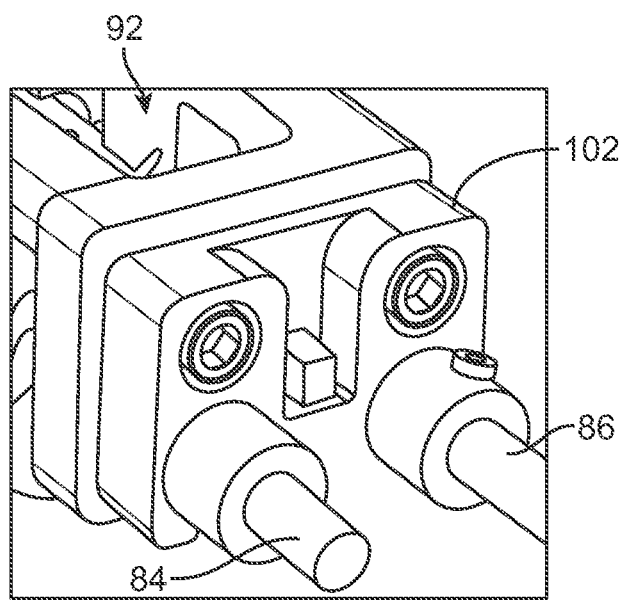
Figure 9:
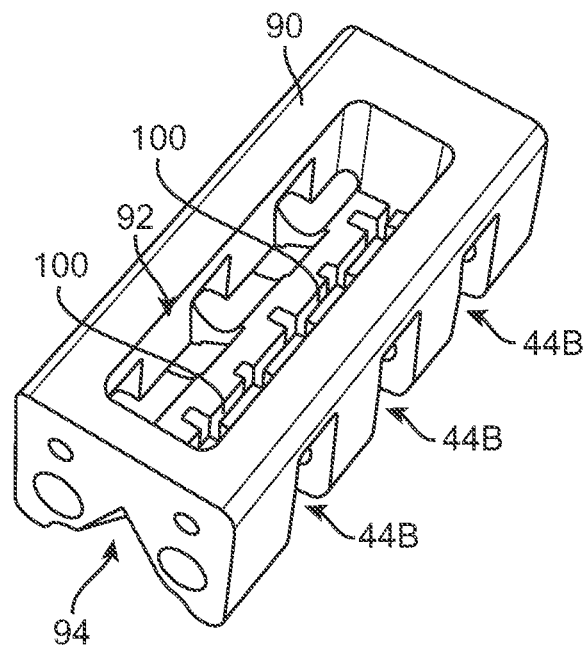
FIGS. 9 and 10 illustrate perspective and end views of the assembly housing from the variation of FIGS. 7A to 7C.
Figure 10:
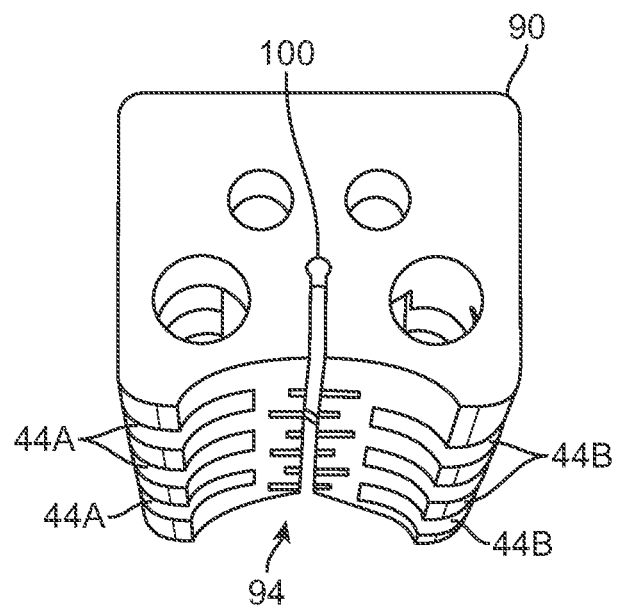

FIGS. 8A and 8B further illustrate detail perspective views of the proximal and distal ends of the assembly. The connection between actuation handle 82 to actuation shaft 84 may be seen while a distal end plate 102 is further shown in FIG. 8B with the actuation shafts 84, 86 passed through the housing 90. The range of motion through which the actuation handles may rotate may be adjusted via any number of mechanisms such as by set screws as shown in this variation. FIGS. 9 and 10 also illustrate perspective and end views of the housing 90 in this variation. The tissue receiving channel 94 is shown as well as the needle guides 44A, 44B for each of the needles. The stylet channel 100 is also illustrated defined through the length of the housing 90 where the stylet channel 100 is coincident with the longitudinal axis in proximity to where each of the needle distal tips converges.

Figure 11A:
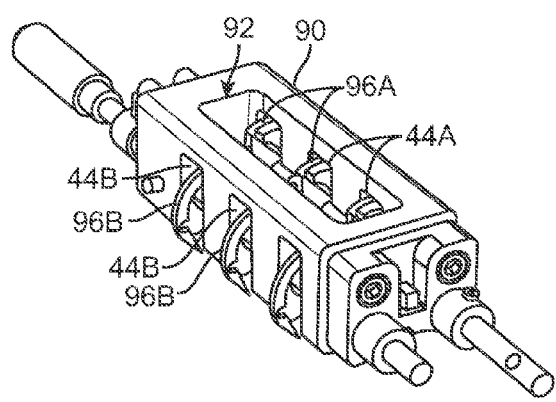
FIGS. 11A and 11B illustrate perspective and detail views of the assembly of FIGS. 7A to 7C.
Figure 11B:
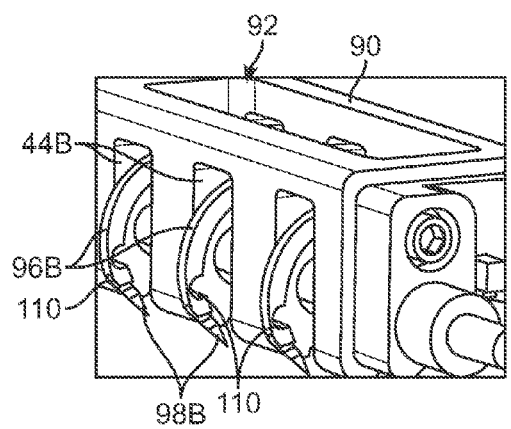

FIGS. 11A and 11B illustrate perspective views of the housing 90 where each of the needles is partially deployed. The curved or arcuate needles are shown as having been at least partially rotated from their delivery configuration to their deployed configuration. The needle piercing tips are also shown with a stylet clearance slot 110 defined along each needle body proximal to the piercing tip. The stylet clearance slot 110 provides for passage of the stylet 89 in proximity to the deployed needles when the stylet 89 is used to pass the suture through the suture loops passed by each needle through the tissue, as described in further detail below.

Figure 12:
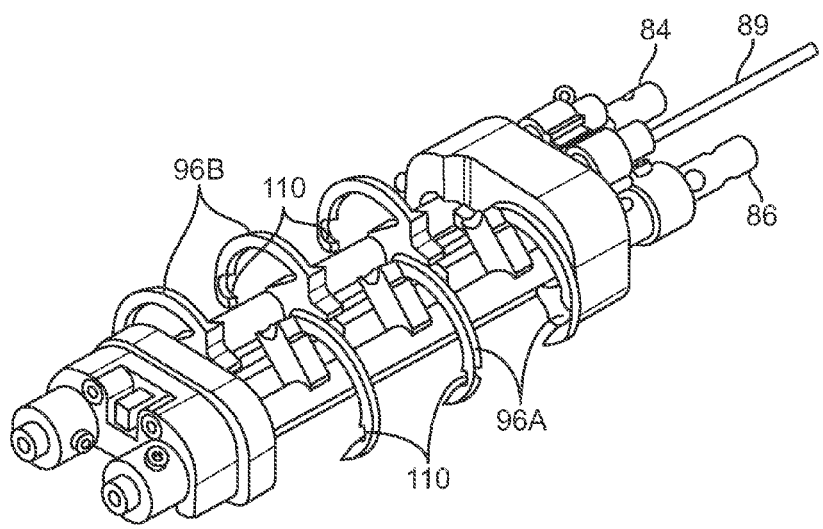
FIG. 12 illustrates a perspective view of yet another variation of the suture delivery assembly.

FIG. 12 illustrates a perspective view of the needle assembly removed from the housing 90. The individual needles 96A, 96B are shown positioned along their respective needle shafts 84, 86.

Figure 13:
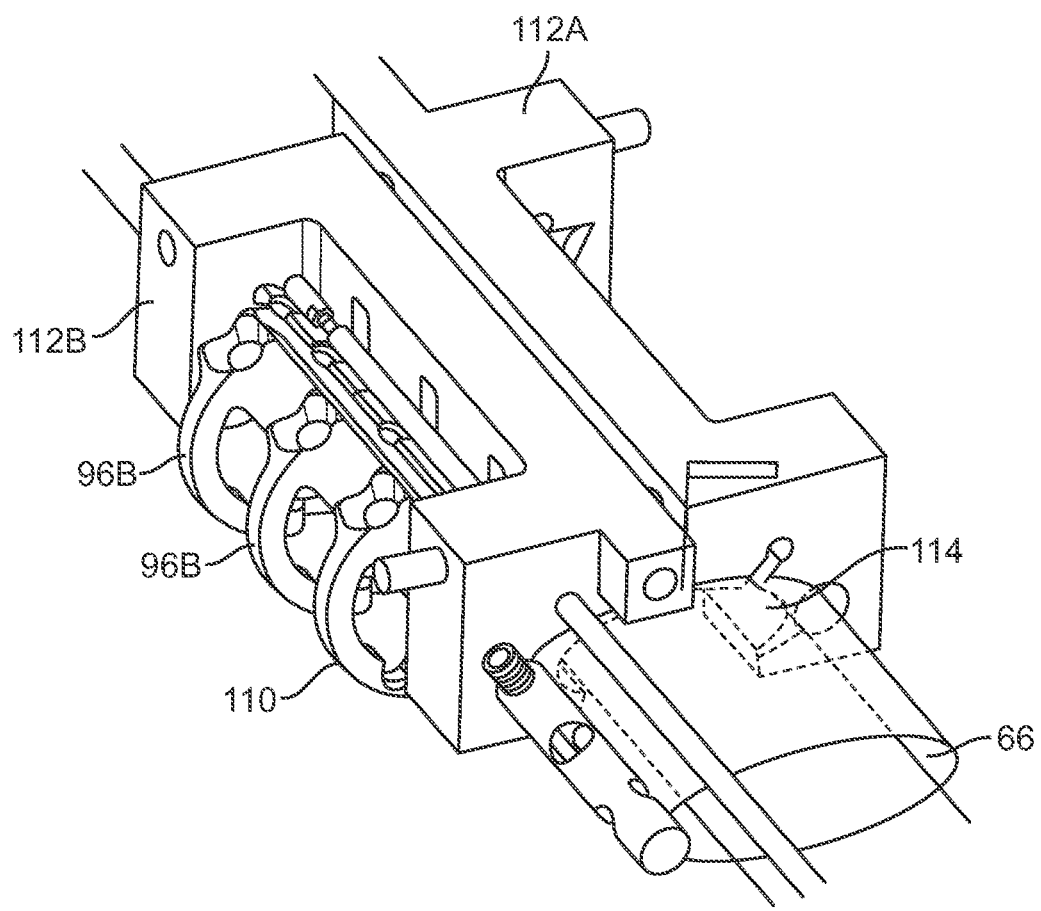
FIG. 13 illustrates a perspective view of yet another variation of the suture delivery assembly.

FIG. 13 illustrates yet another variation of an adjustable housing assembly which has two adjacent housing assemblies 112A, 112B defining a tissue receiving channel 114 therebetween. The housing assemblies 112A, 112B may be movably adjusted relatively away or towards one another to accommodate various size tissues 66 to be treated. Moreover, the adjustability of the housing assemblies 112A, 112B may also allow for the tissue 66 to be stabilized relative to the housing assemblies 112A, 112B by temporarily clamping the assemblies upon the tissue 66 while the needles and suture are driven into and through the tissue 66.

Figure 14:
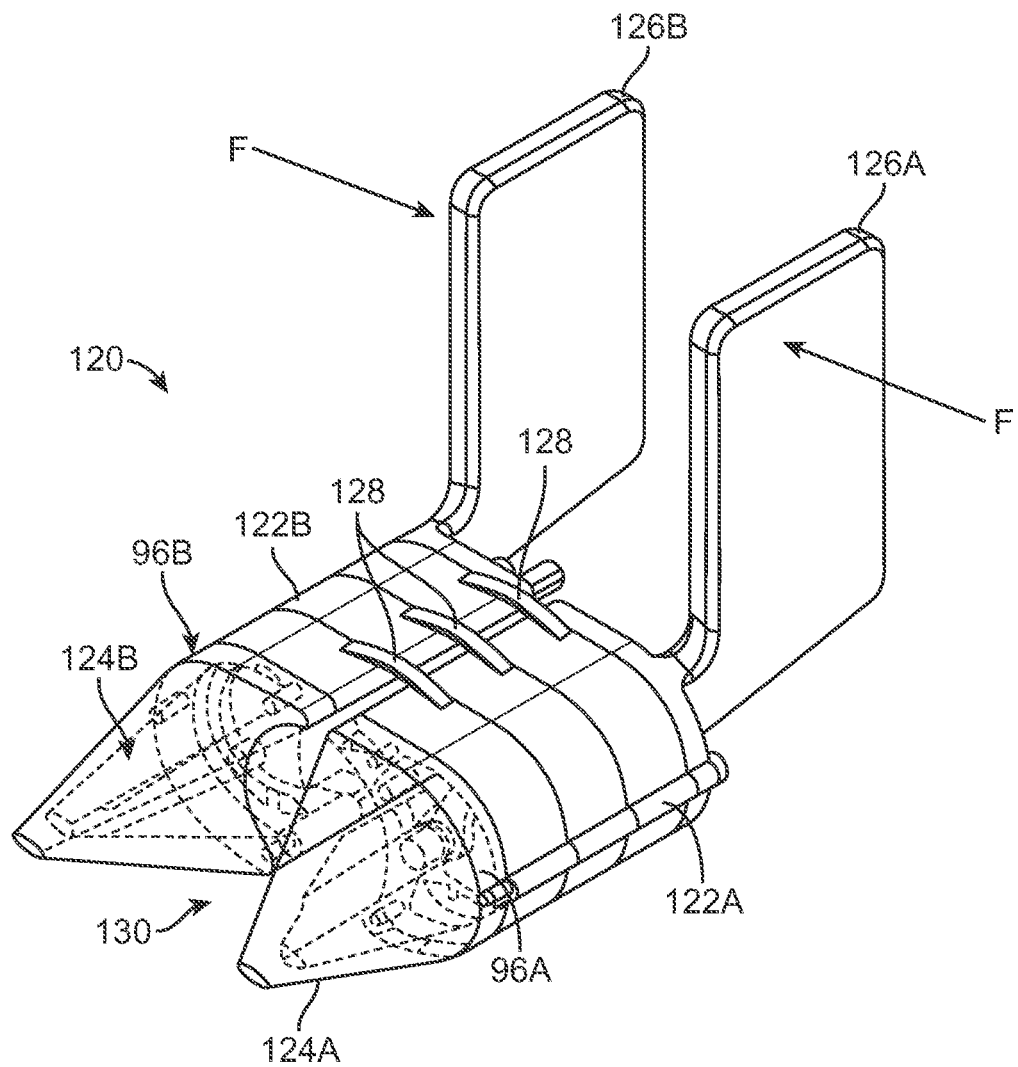
FIG. 14 illustrates a perspective view of yet another variation of the suture delivery assembly having a dual housing embodiment.

FIG. 14 illustrates another variation in the perspective view of tissue repair assembly 120. This variation utilizes an adjustable dual housing configuration having a first adjustable housing 122A and a second adjustable housing 122B which are coupled to one another via one or more biasing members 128, e.g., one or more springs. Each of the adjustable housing 122A, 122B may present a rounded or curved atraumatic outer surface with a first tapered member 124A positioned upon a distal end of the first housing 122A and a second tapered member 124B positioned upon a distal end of the second housing 122B. The tapered members 124A, 124B may present a smooth angled surface to facilitate the insertion of the assembly 120 through the incision and into the subcutaneous tissue space. The proximal end of the housing 122A, 122B may have any number of actuatable handles attached although the handles are shown with a respective first handle 126A and second handle 126B extending transversely relative to the housing 122A, 122B.

The adjustable tissue receiving channel 130 may be defined between each of the first and second housing 122A, 122B where a force F (such as by manual manipulation by the practitioner) may be applied to press the first and second handles 126A, 126B towards one another, as indicated by the direction of force application. Force F applied to the handles 126A, 126B may urge the housing 122A, 122B to pivot about biasing members 128 away from one another and enable the housing 122A, 122B to adjust to accommodate various size tissues positioned along the tissue receiving channel 130. Because the one or more biasing members 128 may apply a constant biasing force, the housing 122A, 122B may clamp upon the tissue within the receiving channel 130 to temporarily secure the tissue and inhibit relative movement between the tissue and housing during needle and suture deployment.

Figure 15A:
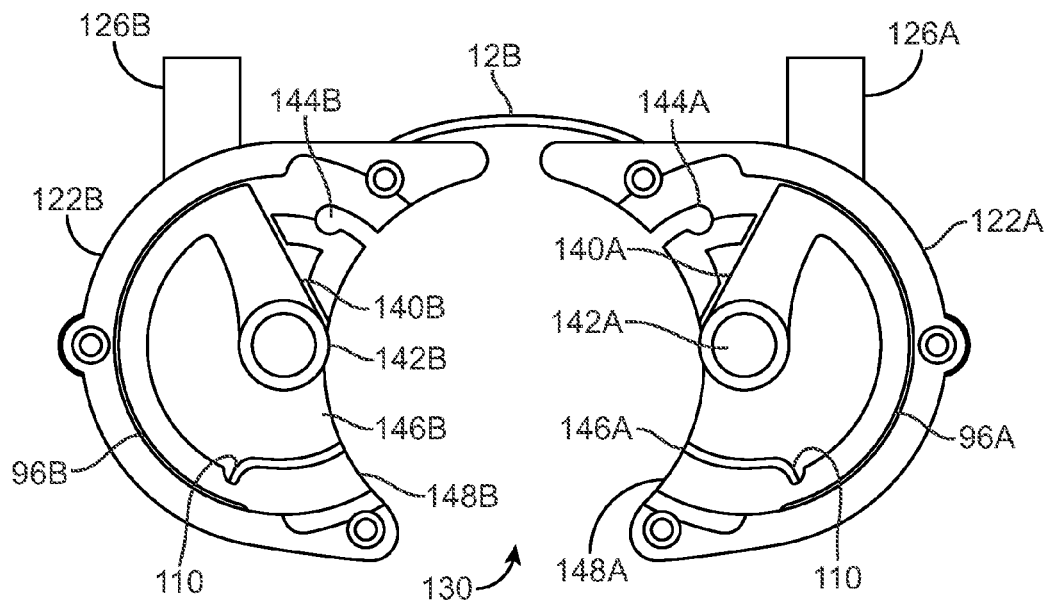
FIGS. 15A and 15B illustrate partial cross-sectional end views showing the adjustment between the dual housing and the actuation of the respective needle assemblies.
Figure 15B:
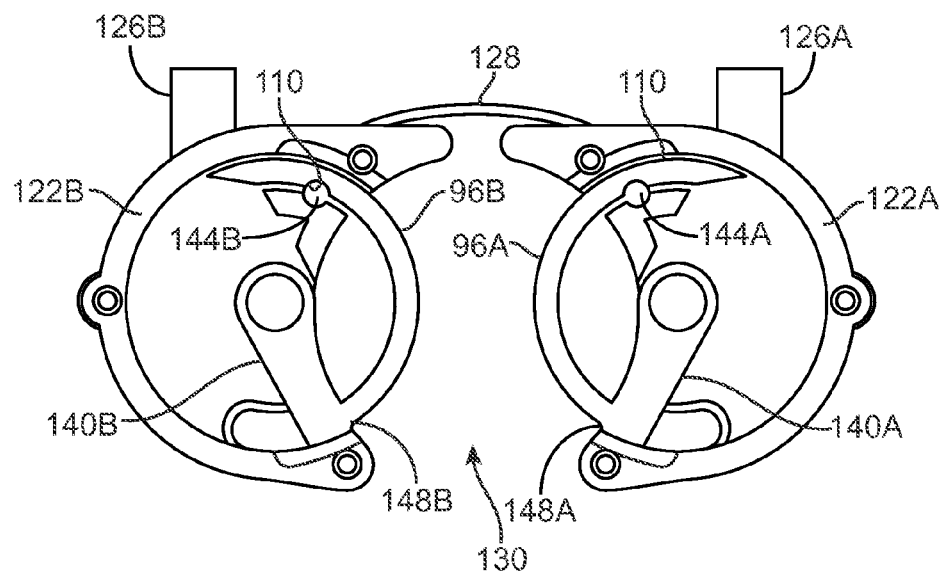

FIGS. 15A and 15B illustrate partial cross-sectional end views of the tissue repair assembly 120 to show how the housing 122A, 122B may be adjustable relative to one another as well as to show how the needle assemblies may traverse through the tissue receiving channel 130. As shown, the needles 96A, 96B may be formed to have a curved or arcuate shape, e.g., semi-circular, where the needle body curves into a piercing distal tip from a proximal end which forms a needle support arm 140A, 140B configured to extend transversely relative to the needle body. The needle support arm 140A, 140B may define an opening through which the actuation shaft passes. During device insertion and placement within the patient, the needles 96A, 96B may be retracted into their delivery position where the needles 96A, 96B are contained entirely (or at least partially) within their respective housing 122A, 122B, as shown in FIG. 15A.

Once the repair device has been inserted in proximity to the tissue region to be treated, the housing 122A, 122B may be articulated via actuation handles 126A, 126B such that the housing 122A, 122B pivots about the one or more biasing members 128 to place the presentation surfaces 146A, 146B defining the tissue receiving channel 130 securely around the tissue of interest. With the tissue positioned within the tissue receiving channel 130, the housing 122A, 122B positioning relative to the tissue may be further adjusted, if so desired. Each of the needles 96A, 96B may have one or more lengths of suture positioned along each needle body and between each adjacent needle, as described in further detail below. Once the device has been desirably positioned relative to the tissue, the needles 96A, 96B may be actuated (simultaneously or sequentially, as described above) such that the needles 96A, 96B are rotated by the actuation shafts 142A, 142B. The piercing tips of the needles 96A, 96B may accordingly exit the needle openings 148A, 148B defined along the presentation surfaces 146A, 146B and traverse through the tissue receiving channel in a circular curve or arc trajectory, as shown in FIG. 15B.

As the needles 96A, 96B traverse through the channel 130 and tissue, the needles may pass the suture loops through the tissue and into proximity to the stylet channels 144A, 144B defined longitudinally through respective housing 122A, 122B. As previously described, the needles 96A, 96B may define a notched or cut-out section as a stylet clearance slot 110 which aligns with the stylet channels 144A, 144B when the needles 96A, 96B have been fully rotated into their deployed configuration. Once the needles 96A, 96B have carried the suture lengths and suture loops through the tissue and into proximity to the stylet channels 144A, 144B, the stylet (which carries a length of the suture) may accordingly be passed through the stylet channel 144A, 144B to route the suture through the suture loops for further tightening of the suture upon the tissue. Once the suture loops have been passed via the needles 96A, 96B, the needles may be retracted proximally back through the tissue and into the housing 122A, 122B for disengaging the tissue and subsequent removal of the device from the tissue region.

Figure 16A:
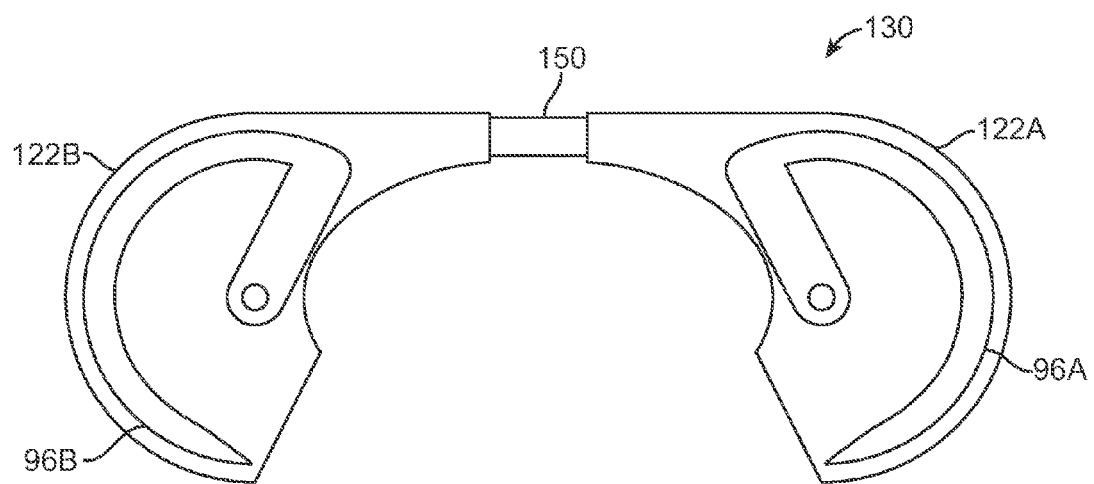
FIGS. 16A and 16B illustrate partial cross-sectional end views of another variation for adjusting the dual housing.
Figure 16B:
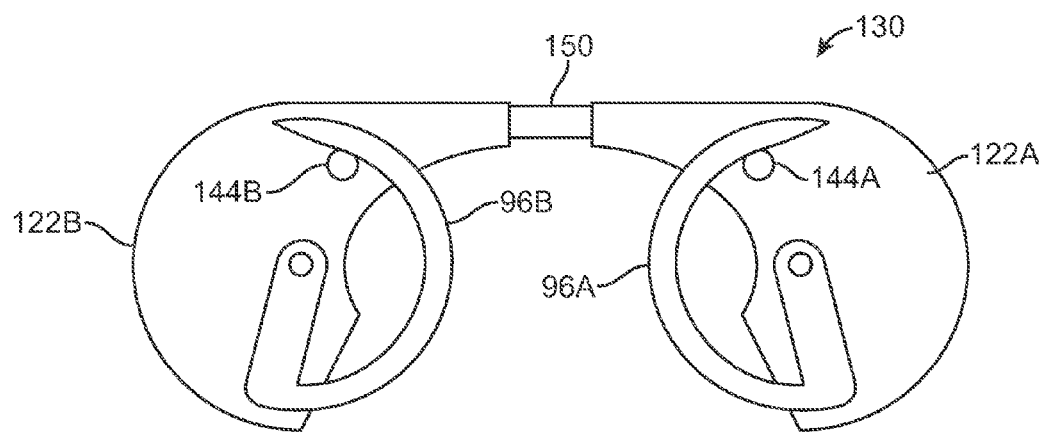

FIGS. 16A and 16B show partial cross-sectional side views of another variation where the respective housing 122A, 122B may be coupled to one another and adjusted accordingly via an adjustable hinge or pivot 150. The hinge or pivot 150 may allow for the pivotal and/or translational adjustment of the housing 122A, 122B relative to one another, as shown in this example.

Figure 17:
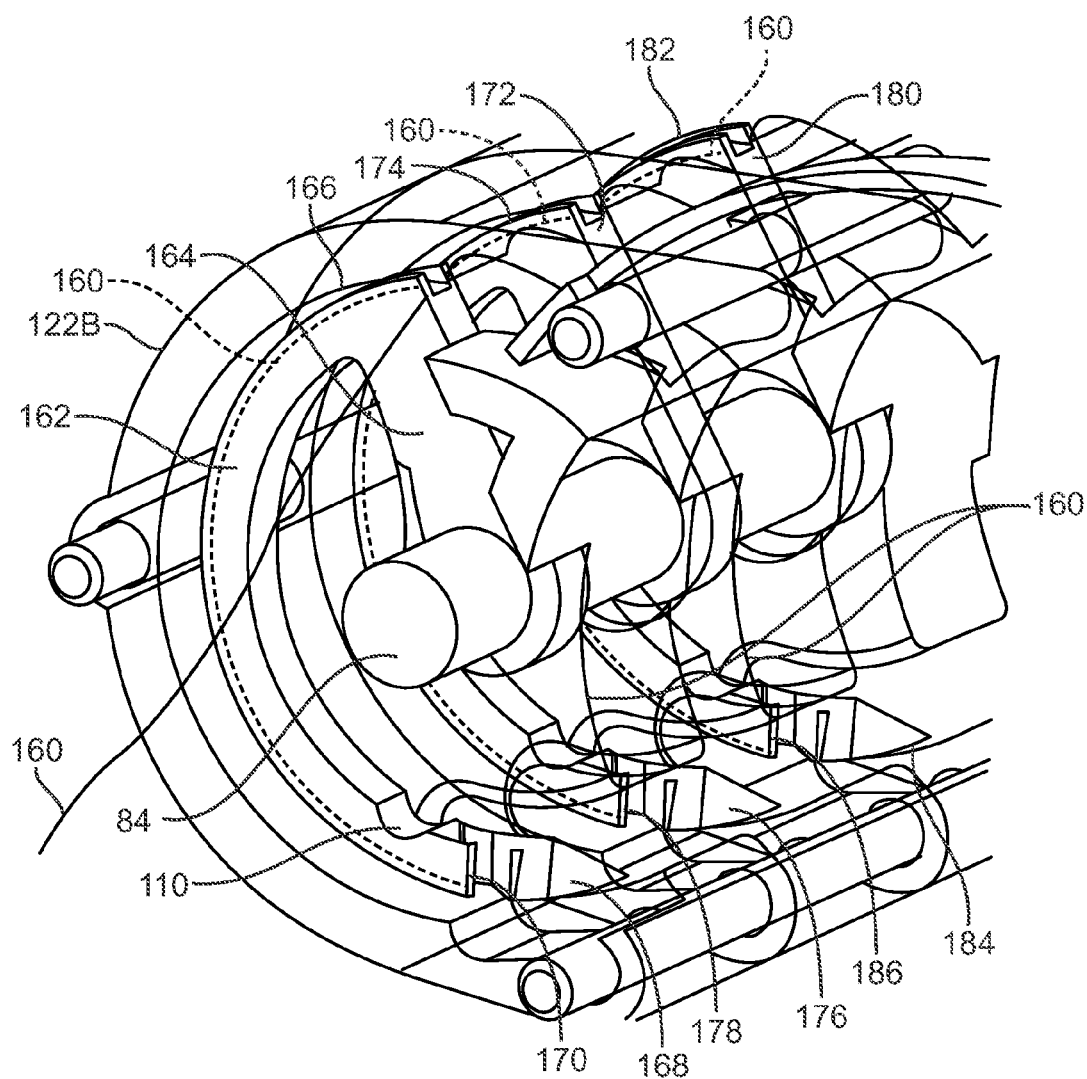
FIG. 17 illustrates a detail perspective view of one example for routing the suture through the needle assembly between each adjacent needle.

Turning now to FIG. 17, an example of how the suture may be routed through the housing and between each adjacent needle is shown in the perspective assembly view. As described herein, each of the needles may carry a length of suture and/or suture loops for passage through the tissue. The suture may be comprised of individual lengths of suture or a single contiguous length of suture may be routed through the housing between each adjacent needle. In this variation, with the needle assembly retracted in its delivery configuration within the housing 122B, a single length of suture 160 may be routed towards a proximal end of a first needle 162 which may define a suture guide channel 166 along an outer circumference of the needle from where the needle body extends from the needle support arm 164 towards the needle tip 168. The suture 160 may be guided along this suture guide channel 166 such that the suture 160 extends along the needle body towards a suture guide exit 170 which may comprise a channel or groove along the needle body proximal to the needle tip 168. Although the suture guide exit 170 is shown as a channel which is transverse to the needle body, other configurations may be utilized.

As the needle rotates into its deployed configuration, the suture guide channel 166 and suture guide exit 170 helps to maintain the suture position along the needle body, particularly as the needle and suture passes through the tissue. Moreover, the suture guide exit 170 may help to push the suture 160 through the tissue and then enables the suture 160 to be released from the needle guide exit 170 as the needle is retracted to leave the suture 160 length behind.

Once the suture 160 passes through the suture guide exit 170 of first needle 162, the suture 160 is further routed towards the adjacent second needle 172. The suture 160 may enter suture guide channel 174 and pass along the needle body towards the suture guide exit 178 of the second needle proximal to the needle tip 176. The suture 160 may then continue to the adjacent third needle 180 where the suture similarly enters the suture guide channel 182. As with the second needle 172, the suture 160 may be routed along the suture guide channel 182 until it passes through suture guide exit 186 proximal to the needle tip 184. The suture 160 may then be further routed proximally where a terminal end (or a portion) of the suture 160 may be passed along the stylet 89 for passage through the stylet channel and for tightening to the tissue.

Figure 18:
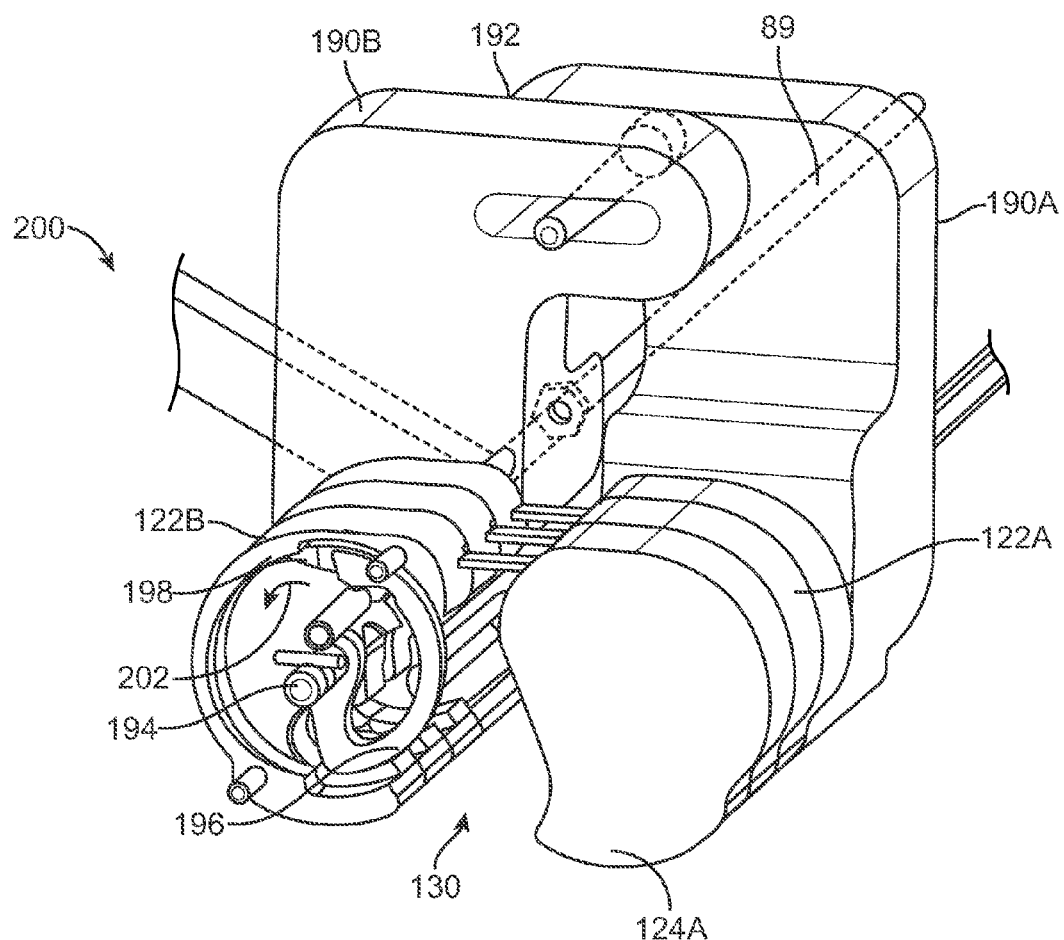
FIG. 18 illustrates a perspective view of another variation of the dual housing embodiment with the structure partially removed for clarity.

FIG. 18 illustrates a partial assembly view of another variation of the tissue repair assembly having a dual housing 122A, 122B configuration. Each housing 122A, 122B is shown extending from a respective first housing support 190A and second housing support 190B which are pivotably coupled to one another via a pivot 192. The first and second housing support 190A, 190B may enable the housing 122A, 122B to be adjusted relative to one another while the actuation handle may be coupled to the needle actuation shaft 194 for deploying the needle assemblies.

Also shown is a single needle 196 having piercing tip 198. As the shaft is actuated, as indicated by the direction of handle actuation 200, the corresponding direction of needle actuation 202 illustrates how the one or more needles 196 may be actuated to rotate with shaft 194 to traverse the piercing tip 198 and suture carried by the needle into and through the tissue positioned within tissue receiving channel 130. This variation illustrates an embodiment where each housing 122A, 122B may utilize its own corresponding stylet 89. For a dual housing embodiment, two individual stylets may be used where the needle assembly within a single housing may converge along its respective stylet channel. A single stylet 89 is shown passing through the stylet channel of second housing 122B while the corresponding stylet which passes through the stylet channel of first housing 122A is omitted for clarity only. Hence, each needle assembly within each housing 122A, 122B may deploy a separate length of suture which may be tightened against the treated tissue. Alternatively, a single length of suture may pass through both needle assemblies within each housing 122A, 122B for deploying a single common suture through both needle assemblies.

Figure 19A:
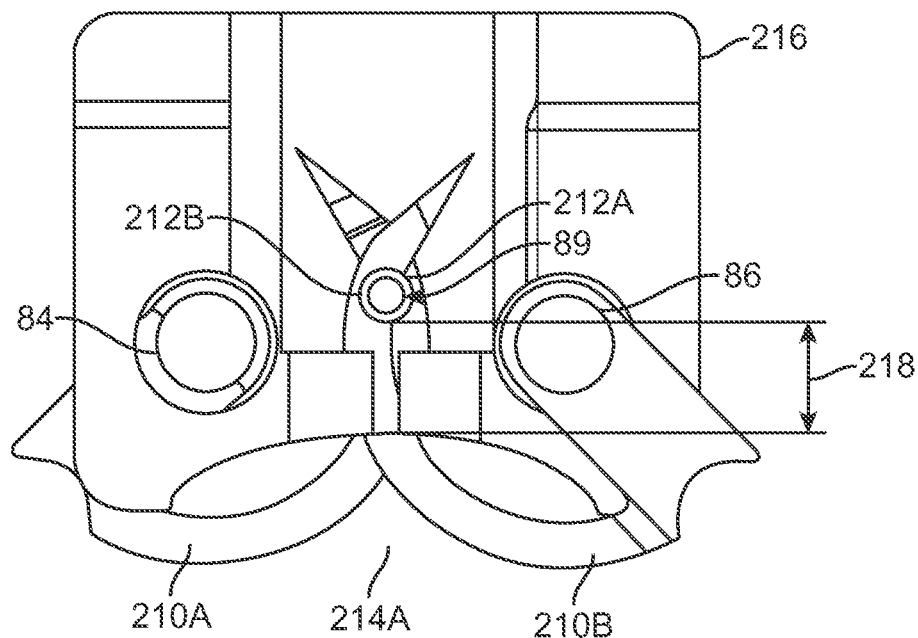
FIGS. 19A and 19B illustrate end and detail end views of an example of the needle clearance and interaction relative to a stylet carrying a length of suture.
Figure 19B:
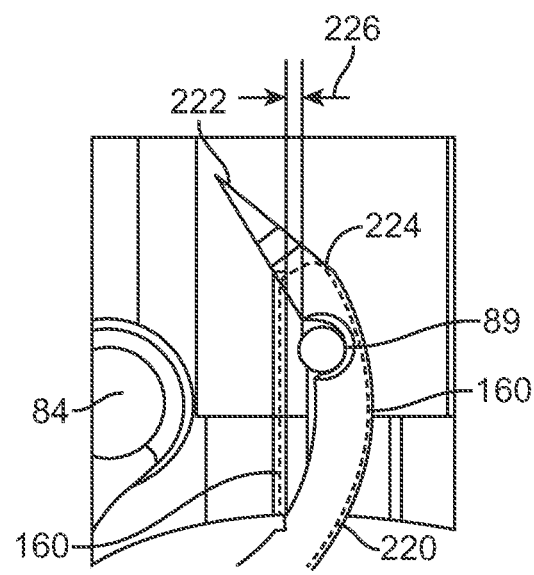

FIGS. 19A and 19B illustrate end views of another variation where the dual needle assemblies may converge along a single stylet channel for use with a single stylet. In this example, as the first needle 210A and second needle 210B are deployed for passage through the tissue receiving channel 214 and the tissue, the first stylet clearance slot 212A of first needle 210A and the second stylet clearance slot 212B of second needle 210B may align with one another within the housing 216 with the stylet channel and stylet 89 which may pass through each of the clearance slots of each needle. The stylet 89 may be separated at a distance 218 between the stylet 89 and the tissue receiving channel 214 to ensure that adequate spacing is provided between the tissue surface and the suture loops for tightening.

Moreover, as shown in the detail end view of FIG. 19B, when the stylet clearance slot is aligned with stylet 89, the suture guide exit 224 proximal to the needle tip 222 may be aligned at a distance from the stylet 89 to ensure that adequate suture-to-stylet separation 226 exists to reduce any risk of the suture 160 catching upon the needle during suture release when the needle with withdrawn proximally. Accordingly, as the suture passes over the suture guide channel 220 along the needle body and exits the suture guide exit 224, the exiting suture 160 may be separated at a distance from the style 89.

Figure 20A:
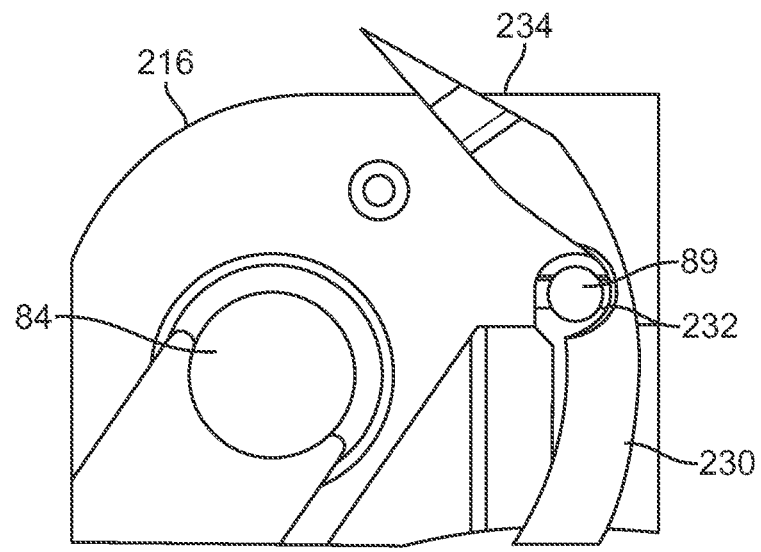
FIGS. 20A and 20B illustrate end views of yet another variation further illustrating an example of how the needle clears the stylet.
Figure 20B:
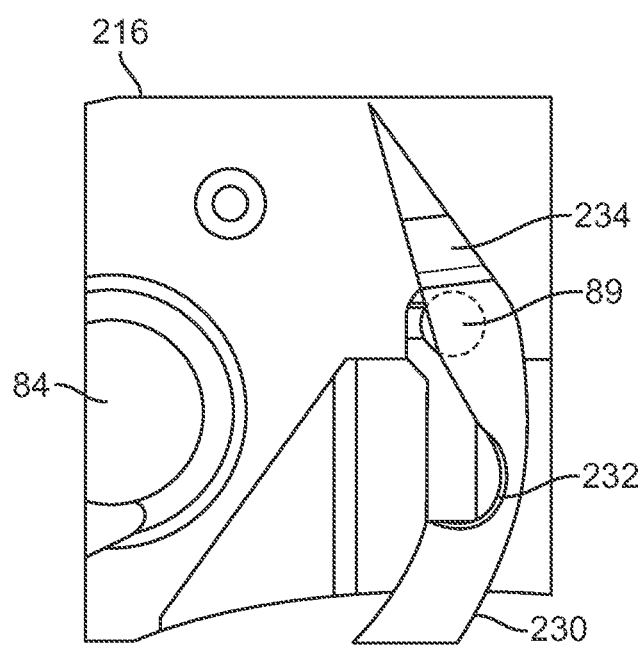

Alternative variations of the needle and suture guide are further shown in the end views of FIGS. 20A and 20B. In this variation, needle 230 is illustrated as having a stylet clearance slot 232 which provides a relatively deeper recess along the needle body as well as a further separation from the suture guide exit 234 to further move the suture away from the stylet to prevent suture puncturing compared to the needle variation of FIG. 19B. The clearance between the suture guide exit 234 and the clearance slot 232 may accordingly be increased as desired.

Figure 21A:
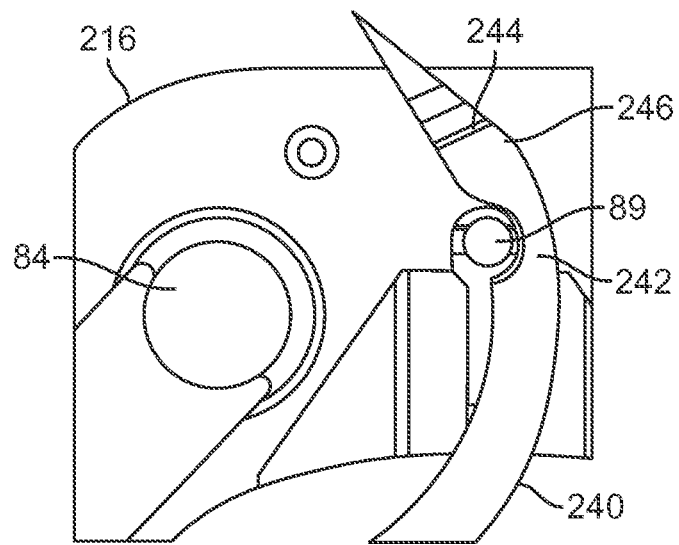
FIGS. 21A and 21B illustrate respective end and detail perspective views of yet another variation of a needle having a groove or channel for suture management.
Figure 21B:
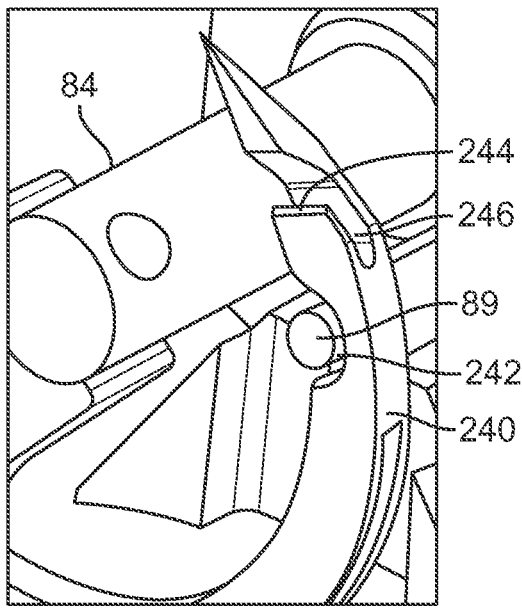

FIGS. 21A and 21B illustrate end and perspective views of yet another needle variation where the needle 240 is provided with a deeper suture groove 246 relative to the needle variation of FIG. 19B. The suture groove 246 may extend between the suture guide exit 244 and stylet clearance slot 242 to further retain the suture to prevent wedging of the suture between the needle body.

Figure 22A:
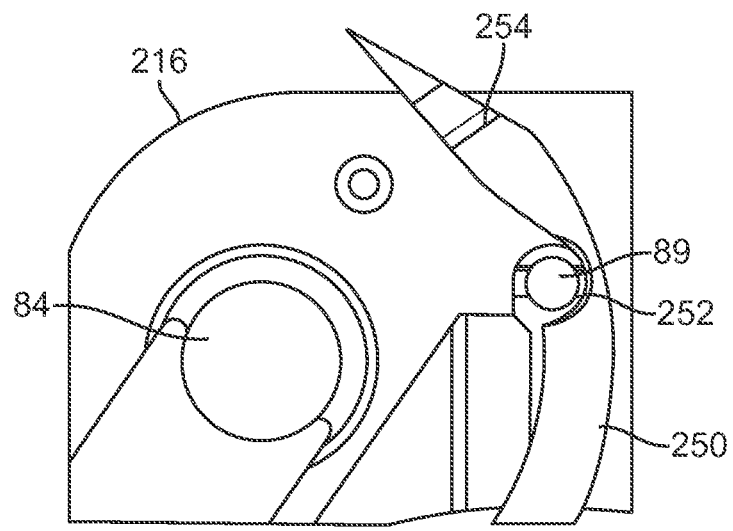
FIGS. 22A and 22B illustrate respective end and detail perspective views of yet another variation of a needle having a suture guide for suture management.
Figure 22B:
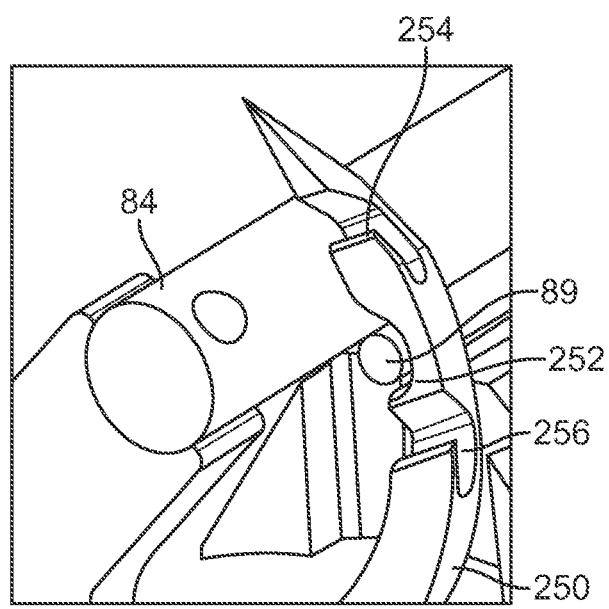

Yet another variation is illustrated in the end and perspective views of FIGS. 22A and 22B which show a needle variation 250 having an additional side cutout to further provide a path for the suture to prevent wedging of the suture. The suture guide exit 254 may be provided distal to the stylet clearance slot 252 but an additional suture groove 256 may be provided along the needle body proximal to the stylet clearance slot 252. The suture may be routed along the outer channel of the needle body and then pass through the suture groove 256 towards an inner portion (e.g., towards the inner diameter) of the needle body where the suture may then pass through suture guide exit 254. Alternatively, the suture may be routed either along the inner diameter or outer diameter of the needle body and pass accordingly through both the suture groove 256 and suture guide exit 254 in an alternating manner.

Figure 23:
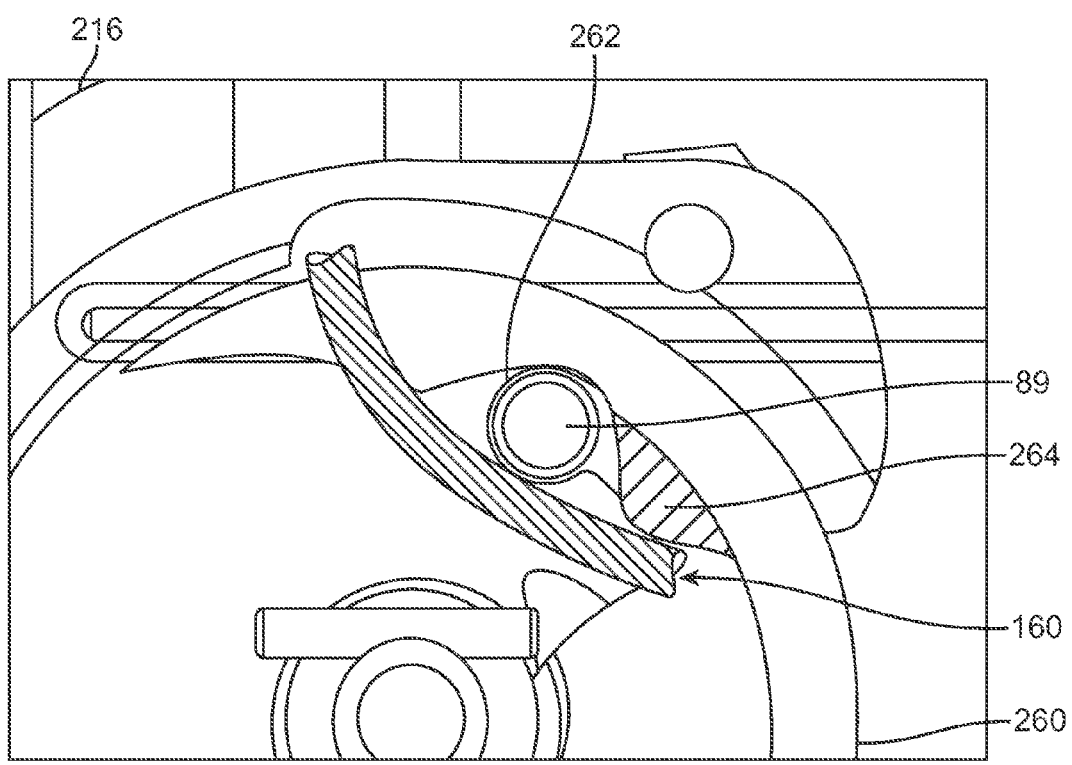
FIG. 23 illustrates a side view of yet another variation of a needle incorporating a projection for proximal to the stylet for facilitating suture management.

In yet another variation, the needle 260 may be provided with a needle projection 264 proximal to the stylet clearance slot 262, as illustrated in the end view of FIG. 23. The needle projection 264 may be an enlarged portion of the needle body extending from an inner diameter of the needle and may function to guide the suture 160 well around the stylet 89 to prevent or minimize contact between the two.

Figure 24A:
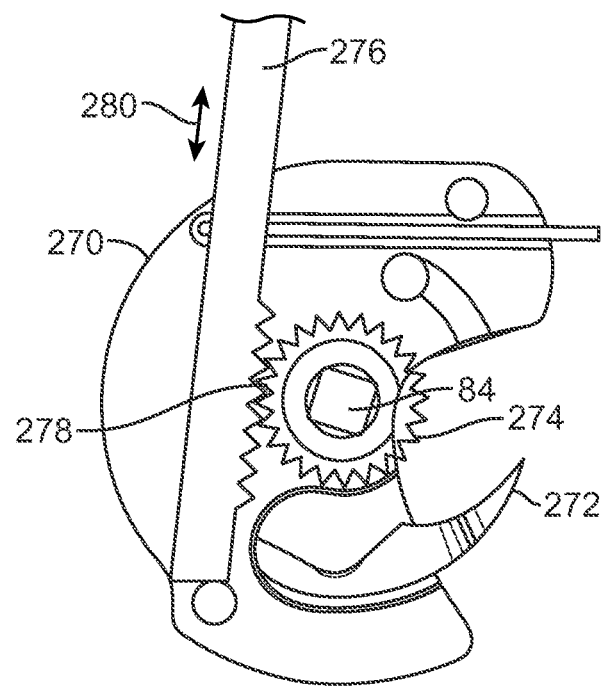
FIGS. 24A and 24B illustrate partial cross-sectional end views of variations for actuating the needle assembly.

Turning now to mechanisms for needle actuation, FIG. 24A illustrates an end view of one variation for rotating actuation shaft 84 to in turn rotate the needle assembly 272 within housing 270. An actuation handle may be directly coupled to a proximal end of the actuation shaft 84, as described above, but another variation may utilize a pinion gear 274 attached to a portion of the actuation shaft 84. A rack 276 attached to an actuation handle may have one or more gear teeth 278 which may be operatively coupled to the gear teeth of pinion gear 274. As the rack 276 is translated along the direction of translation 280 by the actuation handle, the pinion gear 274 may rotate accordingly to deploy and/or retract the needle assembly depending upon the direction of translation 280.

Figure 24B:
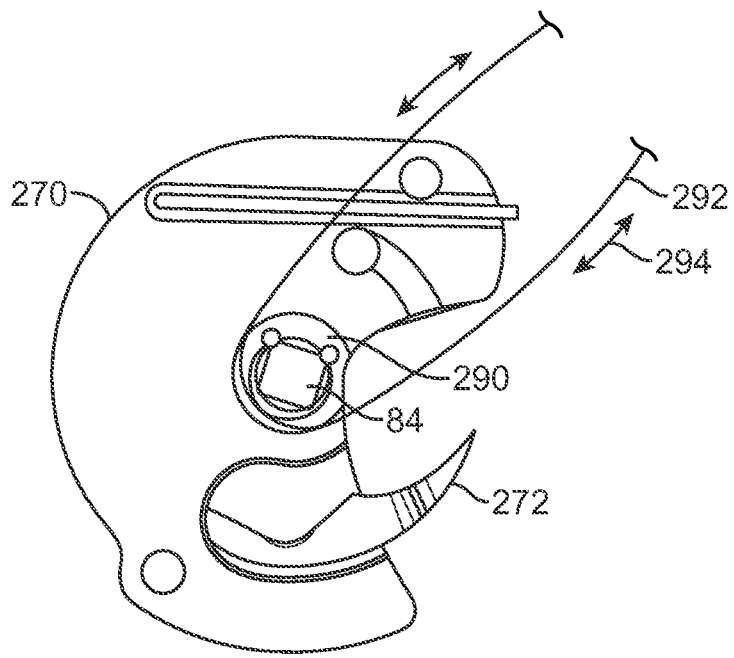

FIG. 24B illustrates another variation in the end view of actuation shaft 84. In this variation, at least one cable 292 may be wound around a pulley 290 attached to actuation shaft 84. The cable 292 may be coupled to an actuation handle which may pull the cable 292 along the direction of actuation 294 to rotate the actuation shaft 84. Deployment and/or retraction of the needle assembly will depend upon the direction of cable actuation.

Figure 25:
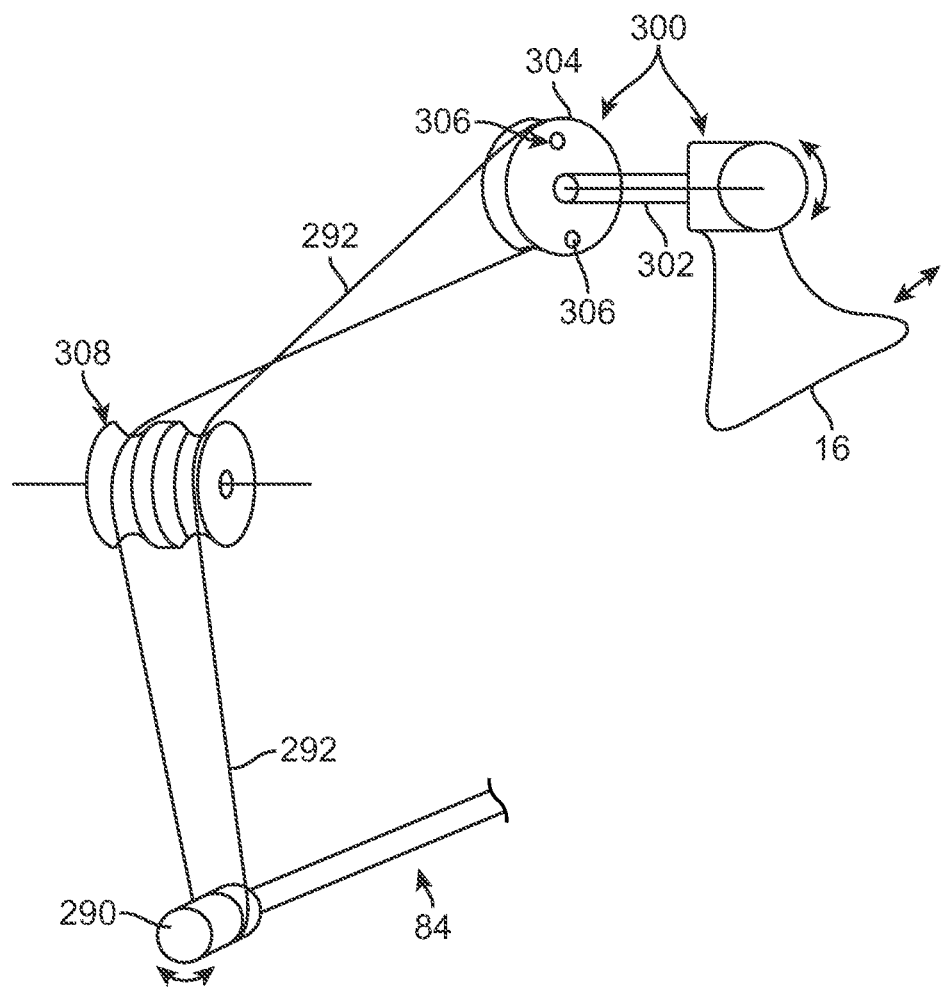
FIG. 25 schematically illustrates an example for transferring an actuation force from the handle to the needle assembly.

FIG. 25 schematically illustrates an example of how a cable assembly may be operatively coupled to an actuation handle for deploying and/or retracting the needle assembly. In this example, the actuation handle 16 may be coupled to a pulley 304 via a shaft 302. Pulley 304 may have cable 292 attached at one or more attachment points 306. The resulting coupled pulleys 300 may thus transfer a rotational movement from the actuation handle 16 into a linear translation along the attached cable 292. The length of the cable 292 may be passed or routed over one or more pulleys 308 to alter the direction of the cable 292 so as to accommodate the configuration of the tissue repair assembly. The cable 292 may be wound or otherwise attached to the actuation shaft 84 via pulley 290, as described above. As the actuation shaft 16 moves the cable 292 in one of two linear directions, the pulley 290 may rotate accordingly and thus rotate actuation shaft 84 in a corresponding manner to deploy and/or retract the needle assemblies.

Figure 26A:
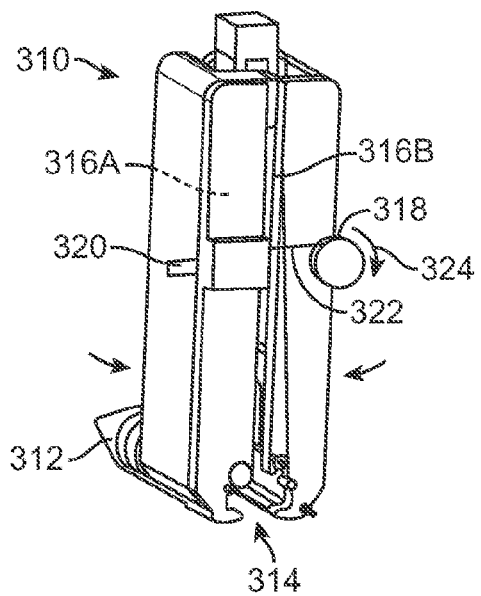
FIG. 26A illustrates a perspective view for one variation of a handle assembly for securing the suture delivery assembly to the tissue to be treated via a cable tightening mechanism.

Aside from the rotation of the needles, the handle assembly 310 may itself be adjustable to facilitate placement and securement of the suture assembly relative to the tissue. FIG. 26A illustrates a perspective view of one variation for temporarily securing the handle assembly 310 upon a portion of tissue. In this variation, the suture delivery assembly 312 may define the tissue receiving channel 314 between the housing members. Each housing member may be attached to a first handle portion 316A and a second handle portion 316B within a housing. A wire or cable 322 may be attached to each of the handle portions 316A, 316B where a first end of the wire or cable 322 is attached to an actuator 318, shown as a rotatable knob in this variation, and the second end of the wire or cable 322 may be an attached to an attachment point 320 along at least one of the handle portions 316A, 316B.

Once the tissue has been desirably positioned along tissue receiving channel 314, the actuator 318 may be rotated in the direction of actuation 324 to tighten the wire or cable 322 and draw the handle portions 316A, 316B towards one another and thereby securing the suture delivery assembly 312 upon the tissue region, as indicated by the arrows.

Figure 26B:
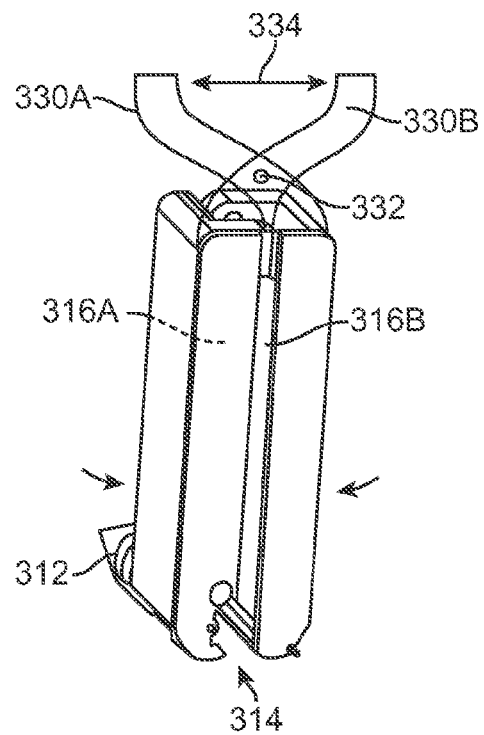
FIG. 26B illustrates a perspective view for another variation for securing the device to the tissue via a squeezable handle.

FIG. 26B illustrates another variation where the handle portions 316A, 316B may be attached to a respective first scissor handle 330A and a second scissor handle 330B which may be rotationally coupled to one another via a pivot 332. As the scissor handles 330A, 330B are squeezed along the direction of actuation 334, the handle portions 316A, 316B may correspondingly clamp upon the tissue region. Movement of the scissor handles 330A, 330B in the opposite direction may correspondingly release the handle portions 316A, 316B from the tissue region.

Figure 26C:
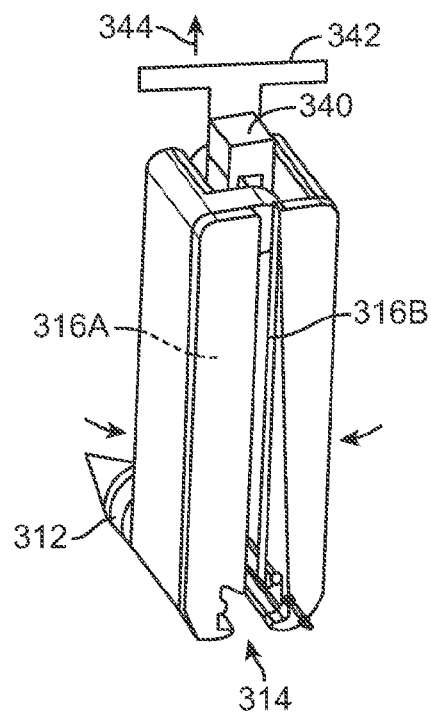
FIG. 26C illustrates a perspective view for another variation for securing the device to the tissue via a translatable handle.
Figure 26D:
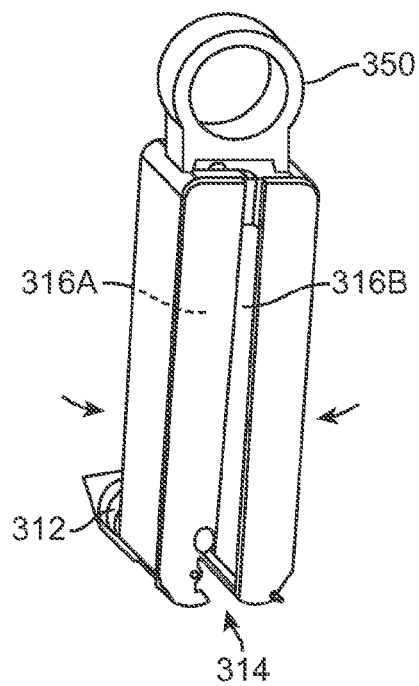
FIG. 26D illustrates a perspective view for another variation for securing the device to the tissue via a ring handle.
Figure 27:
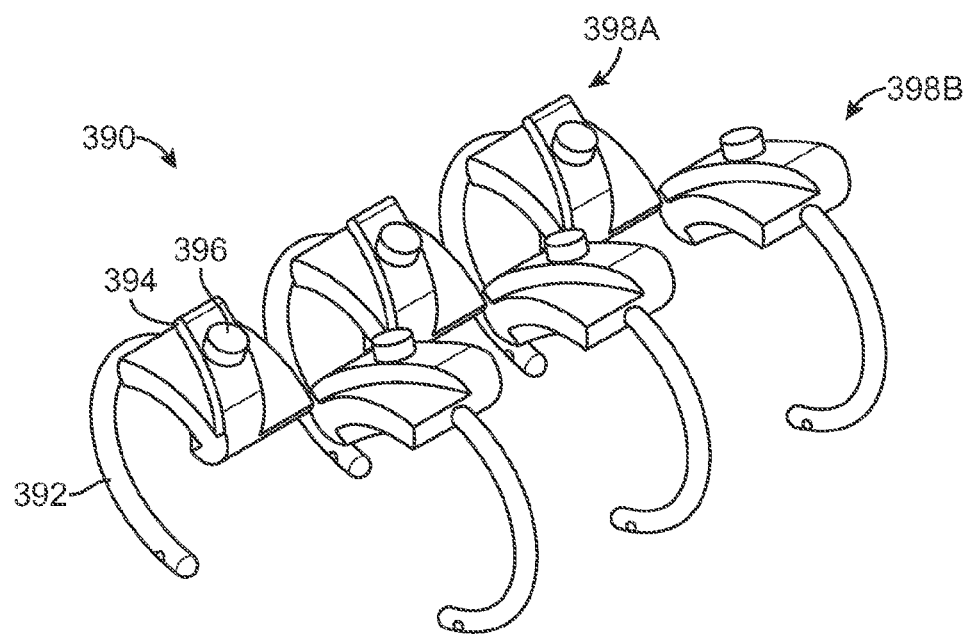
FIG. 27 illustrates a perspective assembly view of another variation of the needle assembly and the respective relative placement.

FIG. 26C illustrates a perspective view of yet another variation where a handle actuation member 340 may be attached to handle portions 316A, 316B. An optional handle 342 may be attached to member 340 such that as the handle 342, e.g., pulled in the direction of actuation 344, the member 340 may function to draw handle portions 316A, 316B towards one another to secure the assembly onto the tissue region. FIG. 26D shows another variation where the handle 342 may be replaced with a ring handle 350.

With respect to the variations shown in FIGS. 26C and 26D, an example is illustrated in the schematic end view of FIG. 26E showing the degree of movement sufficient for securely placing the suture delivery assembly 312 upon the tissue region within tissue receiving channel 314. The adjustable housing members may move relative to one another when functioning as a clamping mechanism for securing the tissue to be treated. The housing members may thus rotate relative to a rotational point 360 where the rotational radius 362 extends from the rotational point 360 to a longitudinal axis of the tissue repair assembly. The degree of rotation 364 that one housing member may rotationally adjust relative to the remaining housing member may vary to less than about 4 degrees to effectively clamp onto the tissue within tissue receiving channel 314.

To effectuate the rotational adjustment, an example of one mechanism is schematically shown in FIG. 26F which may be integrated into the handle assembly of a tissue repair assembly. The handle actuation assembly 370 may incorporate the handle actuation member 340 which is manipulatable by the user. The actuation member 340 may be pivotably coupled to a first member 372A and a second member 372B via a respective first pivot 374A and second pivot 374B. Each of the first and second members 372A, 372B are in turn coupled to a first handle coupling member 376A and a second handle coupling member 376B which are also coupled to another via a pivot 378. The first and second handle coupling members 376A, 376B may be attached to a respective housing member such that when handle actuation member 340 is translated, each of the first and second members 372A, 372B may be urged along a direction of actuation 380 which in turn forces the first and second handle coupling members 376A, 376B towards one another in the direction of handle clamping 382 as they rotate about pivot 378. This variation is illustrative of one mechanism for actuation the housing assembly while other embodiments are also possible.

Turning now to the needle assemblies, another variation is shown in the perspective view of needle assembly 390 where the needles 392 may extend in a curved or arcuate configuration from a corresponding base 394 having a guide 396 which may project radially for alignment through the needle housing. The number and relative positioning of the needles may be varied although the three needles are shown along each side. The needles are illustrated in a staggered and alternating configuration; however, the needles may be more closely aligned such that the needle tips are immediately adjacent to one another. Alternatively, the needles may be arranged in a staggered configuration farther apart from one another depending upon the desired suturing pattern.

Figure 28:
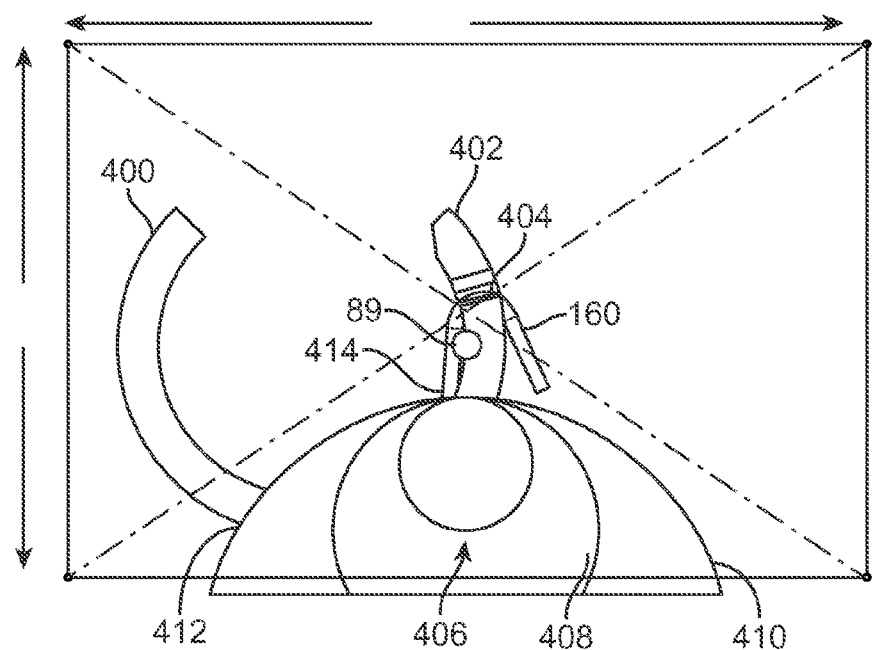
FIG. 28 schematically illustrates an end view of an example of how the needle may be used with a range of tissue sizes.

Regardless of the number of needles used and the relative positioning of the needles, the needles may be configured and positioned relative to the tissue receiving channel such that the needles may penetrate into and through any number of varying tissue sizes. As illustrated in the end view of FIG. 28, an exemplary needle body 400 which is curved or arcuate (as described herein) may be positioned to penetrate a range of tissue sizes. Shown are representative cross-sectional views of tissues of varying sizes which are superimposed upon one another for comparison. For example, a tissue having a relatively small diameter such as a tendon 406 having 0.5 cm diameter is shown in comparison to a tendon 408 having 1 cm diameter as well a tendon 410 having 2 cm diameter. Regardless of the tissue size, the tissue may be positioned within the tissue receiving channel such that when the needle is deployed, its piercing tip 402 may enter the tissue through a tissue entry 412 along a side portion of the tissue and pierce through the tissue at a tissue exit 414 located along a top portion of the tissue where the side and top are relative to the tissue position relative to the tissue receiving channel.

As shown, the needle may pass a length of suture 160 carried via the suture guide exit 404 entirely through the tissue regardless of tissue size. With the suture 160 passed through, the stylet 89 may be introduced through the suture loop formed by the suture 160 and left when the needle piercing tip 402 is retracted and the suture 160 falls out of the suture guide exit 404.

Figure 29:
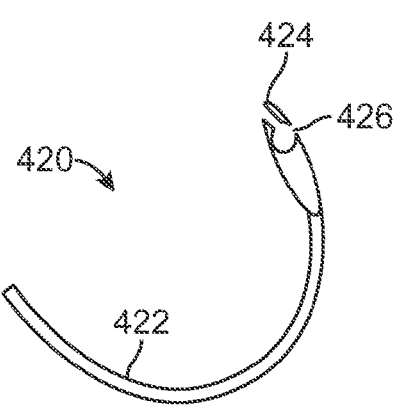
FIG. 29 illustrates a side view of another needle variation having a suture guide.
Figure 30:
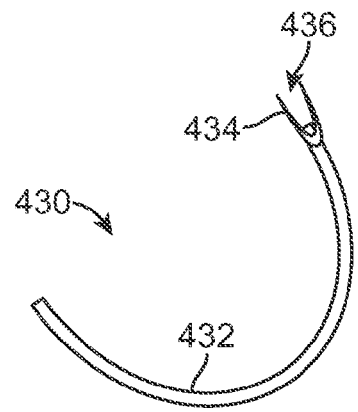
FIG. 30 illustrates a side view of yet another needle variation having a dual piercing tip.

Alternative variations of the needle distal assembly are illustrated in the side views of FIGS. 29 and 30. FIG. 29 shows a needle 420 having a needle body 422 with a piercing tip 424 and a suture guide exit 426 where the suture guide is formed with a split piercing tip 424. FIG. 30 shows a needle 430 having a needle body 432 where the suture guide exit 436 may be formed between a dual-pronged piercing tip 434.

Figure 31A:
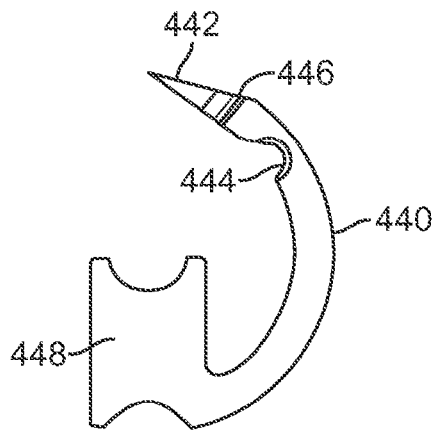
FIGS. 31A and 31B illustrate front and detail side views of another needle variation having a stylet clearance channel and suture guide.
Figure 31B:
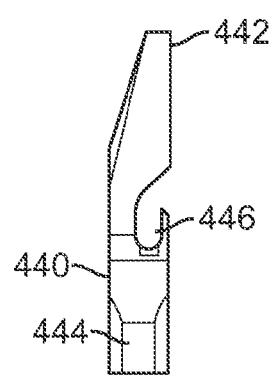

FIGS. 31A and 31B illustrate end and detail side views of yet another variation of a needle where the needle body 440 may curve from a needle base 448 which is configured to abut the needle actuation shaft. The piercing tip 442 extends along a circumference of the needle with the suture guide exit 446 formed proximal to the tip 442 and extends proximally towards the stylet clearance slot 444 where the clearance slot 444 is defined along an inner circumference of the needle body. The piercing tip 442 may be formed over circumference which may extend, e.g., about 180° relative to the needle base 448.

Figure 32A:
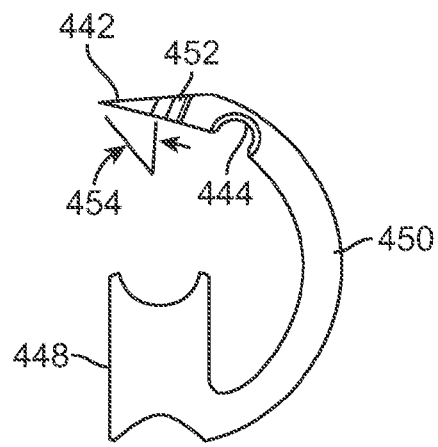
FIGS. 32A and 32B illustrate front and detail side views of another needle variation having a relatively greater angle and needle length.
Figure 32B:
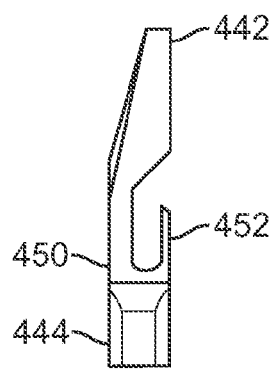

FIGS. 32A and 32B illustrate yet another variation where the needle body 450 similarly curves from the needle base 448 but where the piercing tip 442 is formed at a distal end of a needle body 450 which is relative longer than the needle body 440 of FIG. 31A. The increased angle 454 resulting from the extended needle body 450 may extend, e.g., about 20° more than the needle body 440. Moreover, the suture guide exit 452 may be formed to extend farther proximally within the needle body 450 than the suture guide exit 446 of FIG. 31A to facilitate securement of the suture during passage through the tissue.

Figure 33A:
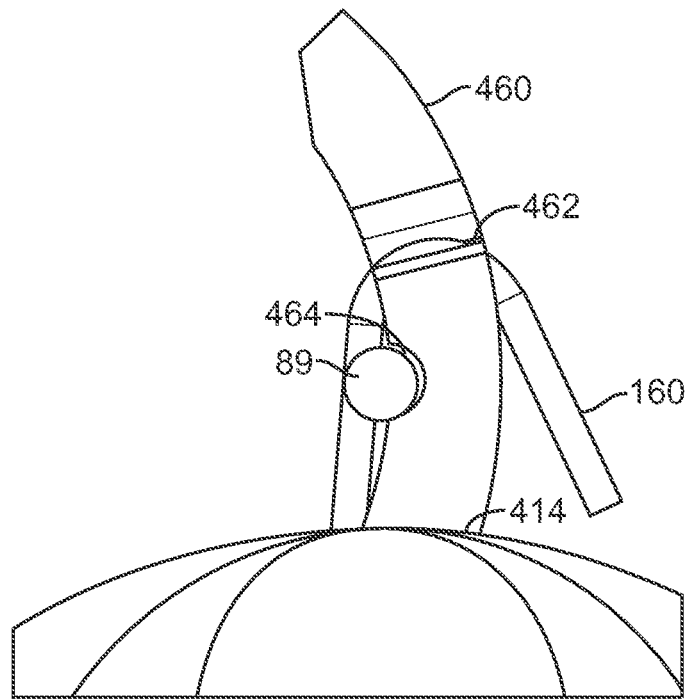
FIGS. 33A and 33B illustrate front and detail perspective views of a needle variation showing how the suture is pulled through the tissue with the suture guide.
Figure 33B:
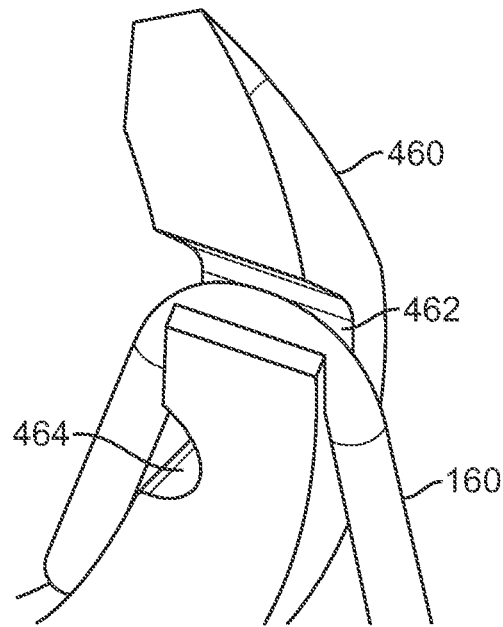

FIGS. 33A and 33B illustrate detail end and perspective views of a variation of the needle to show the relative positioning. With the needle 460 pierced through the tissue, suture guide 462 may be seen pushing the suture 160 length through the tissue to create a suture loop when needle 460 is retracted. The stylet clearance slot 464 provides a relatively small recess for the stylet 89 to pass under the suture loop.

Figure 34A:
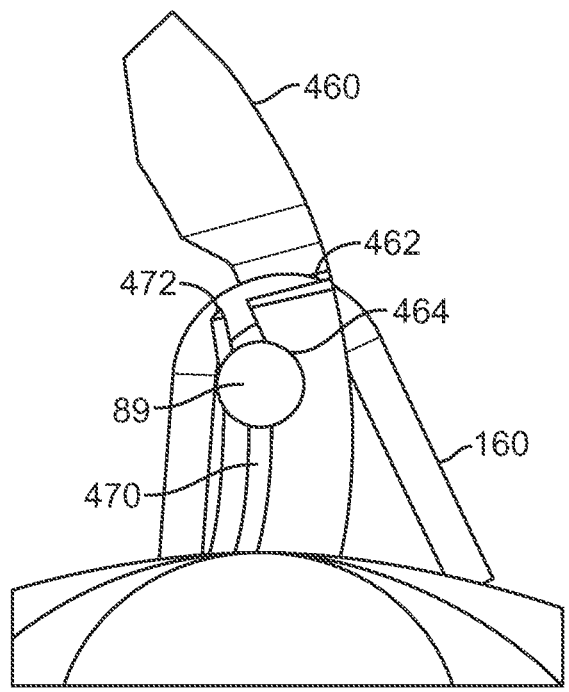
FIGS. 34A and 34B illustrate front and detail perspective views of another needle variation showing a needle having a slot for facilitating the temporary securement and release of the suture through the tissue.
Figure 34B:
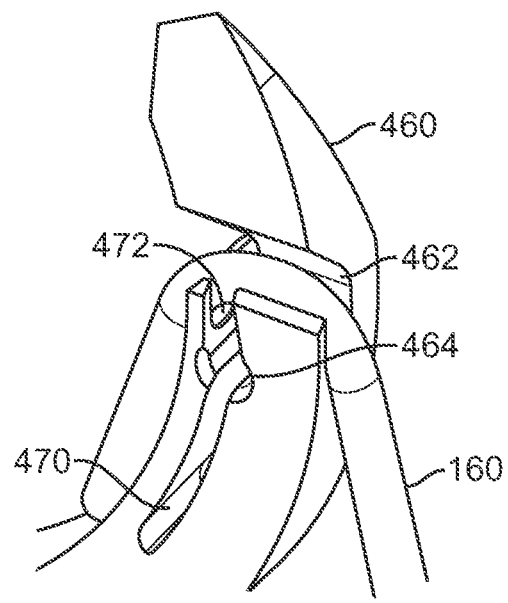

FIGS. 34A and 34B illustrate detail end and perspective views of yet another variation where the needle body may form a slot 470 which extends at least partially along the needle from a slot opening 472 at the suture guide exit 462, through the stylet clearance slot 464, and partially beyond. In this variation, the stylet 89 may be left in place through clearance slot 464 and the needle 460 may be retracted such that the stylet 89 and/or suture along the stylet passes through slot 470 and out through slot opening 472.

FIGS. 35A to 35C illustrate detail end and various perspective views of another variation where the needle 460 may incorporate a suture guidance arm 480 which extends transversely from an inner circumference of the needle body such that the guidance arm 480 projects radially inwards relative to the needle 460 curvature. The suture guidance arm 480 may be comprised of a variety of materials which are elastic or flexible, e.g., Nickel-Titanium alloys such as Nitinol, spring stainless steels, etc. The guidance arm 480 may be positioned proximal to the suture guidance exit 462 and project at a distance to form a curved suture receiving segment 482. With the suture 160 positioned along the suture guidance exit 462, a portion of the suture 160 may pass along the guidance arm 480 which may keep the suture 160 away from the inner surface of the needle body.

As the needle 460 is passed through the tissue with the suture 160, the suture guidance arm 480 may flex or bend proximally along the needle body but when the guidance arm 480 is free from the constraints of the tissue, the guidance arm 480 may reconfigure itself into its unconstrained configuration (as indicated by the direction of arm movement 484) and push the suture 160 out. Likewise, when the needle 460 is retracted proximally through the tissue, the suture guidance arm 480 may flex or bend distally along the needle tip releasing the suture 160 as well as facilitating removal of the needle 460 from the tissue.

FIGS. 36A and 36B illustrate yet another variation in the end and perspective views of a needle 490 which may be formed as having a first retractable petal 492A and a second retractable petal 492B which are apposed to one another to form a stylet channel 496. Each of the petals 492A, 492B may be formed from extensions of the needle body which curve outwardly and then taper towards one another joining along a contact surface 494 to collectively form a piercing tip. The stylet channel 496 defined between the petals 492A, 492B may be sufficiently sized in diameter to receive a stylet 89 passing entirely through the channel 496.

Moreover, each of the petals 492A, 492B may further define a suture guide groove 498 which is defines a curved or arcuate groove or channel for receiving the suture 160, as shown in FIG. 36C. Hence, as the needle 490 passes through the tissue, suture 160 may reside over suture guide groove 498 to be pushed through the tissue. With the needle tip and suture 160 residing through the tissue, the stylet 89 may be passed through the stylet channel 496 and the needle 490 may be retracted relative to the stylet 89 and/or stylet suture such that the petals 492A, 492B open around the stylet 89 and release the stylet 89 and/or suture from the stylet channel 496 thus leaving the suture loop behind.

Figure 37:
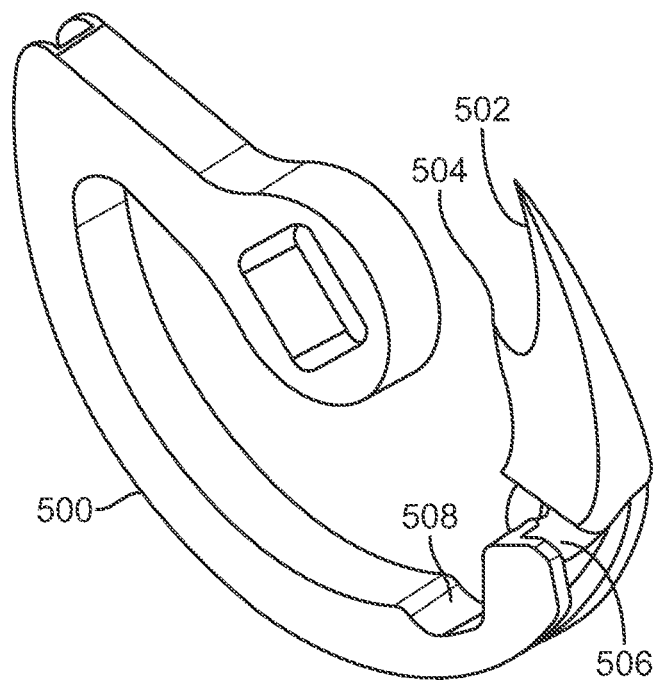
FIG. 37 illustrates a perspective view of another needle variation having a dual piercing and cutting tip.

Yet another variation of the needle is illustrated in the perspective view of FIG. 37 which shows a needle 500 having a piercing tip as well as a cutting edge 502 formed with a secondary cutting edge 504 proximal to the distal tip. The suture guide 506 and stylet clearance slot 508 may be seen proximal to the cutting edges 502, 504. The cutting edge 502 and secondary cutting edge 504 may be formed such that the cutting edges are planarly aligned with the needle body. Moreover, the cutting edges 502, 504 may facilitate the cutting through of the tissue to prevent any elastic effects of the tissue from collapsing the pierced opening.

Figure 38:
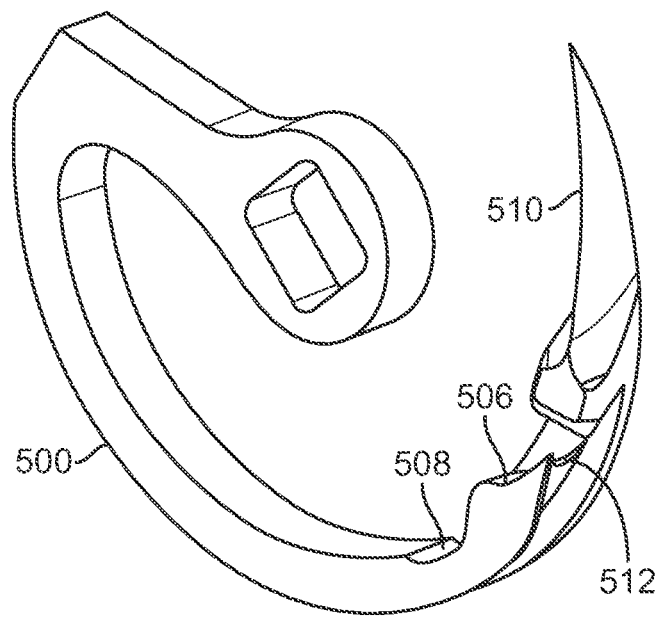
FIG. 38 illustrates a perspective view of yet another needle variation having a cutting edge positioned transversely relative to the needle body.

FIG. 38 illustrates a perspective view of yet another needle variation. In this example, the piercing tip may also incorporate a cutting edge 510 where the edge is formed transversely relative to the needle body. Having the transverse cutting edge 510 may prevent the tissue during needle retraction from catching on the suture guide exit 506. Additionally, a sharpened tip 512 may also be incorporated along the suture guide exit 506 to further cut and minimize any tissue that might otherwise catch on the suture guide exit 506.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A tissue repair system, comprising:
a handle having an actuator;
a suture delivery assembly coupled to the handle and having a dual housing assembly which together defines a tissue receiving channel along the suture delivery assembly;
one or more needles which are curved or arcuate and which are rotatable from a delivery position to a deployment position where the one or more needles are rotatable at least partially through the tissue receiving channel when articulated by the actuator;
one or more lengths of suture which are carried by the one or more needles, wherein the one or more lengths of suture each define a suture loop extendable from a distal tip of the one or more needles; and
one or more stylets which are translatable through the suture delivery assembly,
where the one or more needles each define a clearance slot which is sized to partially receive the one or more stylets when each of the one or more needles are aligned relative to the tissue receiving channel in the deployment position.

2. The system of claim 1 wherein the handle is positioned in a direction opposite to the tissue receiving channel.

3. The system of claim 1 wherein the tissue receiving channel is sized for receiving an Achilles tendon.

4. The system of claim 1 wherein the suture delivery assembly comprises a needle housing having the one or more needles therein aligned to rotate in a direction which is transverse to a longitudinal axis of the suture delivery assembly.

5. The system of claim 1 wherein the suture delivery assembly is removable from the handle.

6. The system of claim 1 wherein the dual housing assembly is adjustable relative to one another.

7. The system of claim 1 wherein the one or more needles comprise a piercing distal tip and a suture guide exit proximal to the tip for temporarily retaining a suture therein.

8. The system of claim 1 wherein the one or more needles comprise at least one cutting edge proximal to a piercing distal tip.

9. The system of claim 1 further comprising a rotatable actuation shaft upon which the one or more needles are positioned.

10. The system of claim 1 wherein the one or more lengths of suture comprise a single common length of suture.

11. The system of claim 1 wherein the one or more stylets comprise a length of suture.

12. The system of claim 1 wherein the one or more needles further define a slot proximal to the clearance slot.

13. The system of claim 1 wherein the one or more needles define a suture guide distal to the clearance slot.

14. A method for repairing a tissue region, comprising:
introducing a suture delivery assembly having a dual housing assembly which together defines a tissue receiving channel therealong through an incision in proximity to a ruptured or torn tendon tissue;
positioning a first portion of the ruptured or torn tissue within the tissue receiving channel;
rotating one or more needles from a delivery position within the suture delivery assembly to a deployment position such that the one or more needles pierce into and through the tissue positioned within the tissue receiving channel, where the one or more needles further pass one or more lengths of suture through the tissue;
advancing at least one stylet through the suture delivery assembly and through at least one stylet clearance slot defined along the one or more needles; and
securing each of the one or more lengths of suture to the first portion of tissue.

15. The method of claim 14 wherein introducing a suture delivery assembly comprises introducing the suture delivery assembly through a single incision along a posterior region of a leg.

16. The method of claim 14 wherein positioning a first portion comprises positioning a first portion of a ruptured or torn tendon within the tissue receiving channel.

17. The method of claim 14 wherein rotating one or more needles comprises actuating a handle attached to a proximal end of the suture delivery assembly.

18. The method of claim 14 wherein rotating one or more needles comprises actuating two or more needles simultaneously.

19. The method of claim 14 wherein rotating one or more needles comprises actuating two or more needles sequentially.

20. The method of claim 14 wherein the one or more needles further define a suture guide along the one or more needles proximal to a distal tip.

21. The method of claim 20 wherein the suture guide forms a suture loop along each of the one or more needles.

22. The method of claim 21 wherein advancing at least one stylet comprises passing a suture length through each of the suture loops.

23. The method of claim 14 further comprising retracting the one or more needles and withdrawing the shaft from the incision.

24. The method of claim 14 further comprising re-introducing the shaft into the incision in proximity to a second portion of the ruptured or torn tissue.

25. The method of claim 24 further comprising approximating the first and second portions of the tissue towards one another and securing the first and second portions.

26. The method of claim 14 wherein rotating further comprises cutting the tissue while rotating the one or more needles.

27. The method of claim 14 further comprising clamping the suture delivery assembly to the ruptured or torn tissue prior to rotating one or more needles.

28. The method of claim 14 wherein advancing at least one stylet comprises clearing a distance between the stylet and the one or more lengths of suture.

29. The method of claim 14 wherein the one or more needles are positioned adjacent to one another in a staggered manner when two or more needles are present within the suture delivery assembly.

* * * * *